US006576418B1

(12) United States Patent
Tryggvason et al.

(10) Patent No.: US 6,576,418 B1
(45) Date of Patent: *Jun. 10, 2003

(54) METHOD FOR DETERMINING THE NUCLEOTIDE SEQUENCE OF THE GENE FOR THE α5(IV) CHAIN OF HUMAN TYPE IV COLLAGEN

(75) Inventors: Karl Tryggvason, Oulu (FI); Sirkka L. Hostikka, Oulu (FI); Jing Zhou, Oulu (FI)

(73) Assignee: BioStratum, Inc., Durham, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/692,989

(22) Filed: Aug. 7, 1996

Related U.S. Application Data

(63) Continuation of application No. 08/346,336, filed on Nov. 29, 1994, now abandoned, which is a continuation of application No. 07/635,475, filed on Dec. 28, 1990, now abandoned, which is a continuation-in-part of application No. 07/377,238, filed on Jul. 7, 1989, now Pat. No. 5,114,840.

(51) Int. Cl.7 .............................. C12Q 1/68; C12P 21/02; C12P 19/34; C07H 21/04

(52) U.S. Cl. ....................... 435/6; 435/69.1; 435/91.1; 435/91.2; 536/23.5

(58) Field of Search ............................... 536/23.4, 23.5, 536/24.3; 530/350, 356; 435/320.1, 6, 69.1, 91.1, 91.2

(56) References Cited

U.S. PATENT DOCUMENTS 4,965,188 A * 10/1990 Mullis et al. ................... 435/6
5,114,840 A * 5/1992 Tryggvason et al. ........... 435/6

OTHER PUBLICATIONS

Brunner, H., et al., (1988) Kidney Int. 34:507–10.*
Pihlajaniemi, T., et al. (1990) J. Biol. Chem. 265:13758–66.*
Spoerel, N.A., et al. (1987) Meth. Enzymol. 152:588–97.*
Zhou, J., et al. (1992) J. Biol. Chem. 267:12475–81.*
Tryggvason, K. (1991) Ann. Med. (Finland) 23:237–9.*
Myers, J. C., et al., (1990) Am. J. Hum. Gent. 46:1024–33.*
Hostikka et al. (Feb 1990) Proc. Natl. Acad. Sci. USA, vol. 87, pp. 1606–1610.*

* cited by examiner

Primary Examiner—Elizabeth Slobodyansky
(74) Attorney, Agent, or Firm—Fay, Sharpe, Fagan, Minnich & McKee, LLP

(57) ABSTRACT

The present invention relates to a method for isolating and identifying the nucleotide sequence of the human gene for the type IV collagen α5(IV) chain. The present invention is directed to the determination of the nucleotide sequence of the gene for the α5(IV) collagen chain in individuals by any method known to the art, e.g. cloning from genomic DNA libraries or amplifying gene regions with the polymerase chain reaction (PCR) and studying their physical properties or nucleotide sequences. In addition, the invention is directed to the use of the nucleotide sequences of the α5(IV) gene to amplify or identify the nucleotide sequences of the α5(IV) gene.

5 Claims, 9 Drawing Sheets

19 ataatcttta tatgcattaa tctttgatgg ataaaattga tatattgtgt tttcacacac
attgattta gGTGATGATG GCTTGCAGGG TCAGCCAGGA CTTCCTGGCC CTACAGGAGA
AAAAGGTAGT AAAGGAGAGC CTGGCCTTCC AGGCCCTCCTG GACCAATGGA TCCAAATCT
TCTGGGCTCA AAAGGAGAGA AGGGGGAACC TGGCTTACCAG gtgagtgaat gaatttatt
tatgaatatt tttcctgata tatctgaagt ttaattttaa atagcatgaa aagtgactt
ataa

18 tttcgtgtga gtccagtgct aatagctcat actatatcag aatatcacca gttcctctaa
ttcacttata gtttaacact tgagtagctt gctttgccaa agttatttca tggatgaata
atatcatcct aacttgcctc ttctactcat tcttggaagG TATACCTGGA GTTTCAGGGC
CAAAAGGTTA TCAGGGTTTG CCTGGAGACC CAGGGCAACC TGGACTGAGT GGACAACCTG
GATTACCAGG ACCACCAGgt aagtgtgata ggccatttgt agcaattgct tagctgacac
tgaattc

17 attttaatga ctatccattc ccatgaaacc agacaacccc aatattgcta cattgtctta
attttaccaa tttgaccttt ctagGTCCCA AAGGTAACCC TGGTCTCCCT GGACAGCCAG
GTCTTATAGG ACCTCCTGGA CTTAAAGGAA CCATCGGTGA TATGGGTTTT CCAGgtgagt
gatgaaaatc ttccaaatat ttagtcccat taatgaaagg tggttcaata tctctttttt
tgtcagaaaa gaggctggtg ttgatagaat cagactgaaa cgatatctga ggtaatcagt
gggtagtgtt ctcttgttac acaaatattt

16 ggagcttttt aaaaatcttt ttgctttgtc atatgcatct tagataatcc acaagtaag
catattttgt aaaatattat atatcacata ttttcaacag GGCCTCAGGG TGTGGAAGGG
CCTCCTGGAC CTTCTGGAGT TCCTGGACAA CCTGGCTCCC CAGGATTACC TGGACAGAAA
GGCGACAAAG GTGATCCTGG TATTTCAAGC ATTGGTCTTC CAGGTCTTCC TGGTCCAAAG
gtaatctttg gcatatagtt ttag

Fig. 2A

15
```
GGTGAGCCTG GTCTGCCTGG ATACCCAGGG AACCCTGGTA TCAAAGGGTTC TGTGGGAGAT
CCTGGTTTGC CCGGATTACC AGGAACCCCT GGAGCAAAAG GACAACCAGG GCTTCCTGGA
TTCCCAG
```

14
```
ttcttttgt cttcactgt ttctatgcta gcactataaa ttgtaagttt gaattgtagc
cttaaagca atgcagtttt tctttcattt ttaaattgag ctctttactc tagGAACCCC
AGGCCCTCCT GGACCAAAAG GTATTAGTGG CCCTCCTGGG AACCCCGGCC TTCCAGGAGA
ACCTGGTCCT GTACgtaagc atgaaaaata acagtttgct gttttataaa actaatgttt
atcatattaa gtttgggaaa gtcaaatcat gttcagctgt gaacattttc aa
```

13
```
agatgctgaa tgactattcc ttattttcat tatcctcctt catattttta taacattttg
tgatccaaag gagtgtctca aaagcaccctt gtttcttttg gataaagaag ggagcatatg
gaagtaaaag ggagttggaa attggaaaac tgggtgtaac ctgctgtact caatttttta
gGTGGTGGAG GTCATCCTGG GCAACCAGGG CCTCCAGGCG AAAAAGGCAA ACCCGGTCAA
GATGGTATTC CTGGACCAGC TGGACAGAAG GGTGAACCAG gtgctgtagt ttttcatttt
tcctattttt ctaattttct ctgtgttgaa tttaacttgc cttttatt
```

12
```
cagttgtatt atccacttga gtttttgttt tgttttgttt tgtactctga cagGTCAACC
AGGCTTTGGA AACCCAGGAC CCCCTGGACT TCCAGGACTT TCTGgtaaac ctaataaaa
catgctaaat caatctataa taaaatgaga ttatttccaa atacatctat ttttccatct
ccaccttta c
```

11
```
ccattaattg ccctaatgta tgtgaatagc taaccttata agcaagcttg taactcggta
ttatttatct tctaattata ctttactttc atagGCCAAA AGGGTGATGG AGGATTACCT
GGGATTCCAG GAAATCCTGG CCTTCCAGGT CCAAAGGGCG GTCCAGCTCT GGAAGGACCT
AAAGGCAACC CTGGGCCCCA AGGTCCTCCT GGGAGACCAG gtatgtccgt gagtggtagg
agaatggtct atttattagt ccatgtattt cgttttgctg gcaggttatt cagtctttaa
gactttagaa ttttccggt gcattggagg atgttaaaaa aaagacttta aaatttgtga
tataacttct tacaagtaaa tagcttggtt catgactaac tccatctatt tccatggttc
taataatttg cttagtaat gcatttt
```

Fig. 2B 10
gaagatgact gatattttaa aagcctgact tttatgctac tcttaacact atactgaaat
gtcgtcattt gctgtggatt attaagGTCT ACCAGGTCCA GAAGGTCCTC CAGGTCTCCC
TGGAAATGGA GGTATTAAAG GAGAGAAGGG AAATCCAGGC CAACCTGGGC TACCTGGCTT
GCCTGGTTTG AAAGGAGATC AAGGACCACC AGGACTCCAG gtaggaaatg gaagtagata
tctgatgaga gaagaatgtg ggtgtttgta ttcaaaatgt gaatc 9
aaactatgaa tcaaggaggt taaataatca actcaattca cacaagataa tataaggcaa
aattgagatt acagtcttgg aagtttgact ctagaaatag tgctatatgc cactatgtaa
ttcttatgcc ctcaatcacc ttcctcccct cgctgcaatt tttttgtaac attaatgatt
ttatttattc agGGTAATCC TGGCCGGCCG GGTCTCAATG GAATGAAAGG AGATCCTGGT
CTCCCTGGTG TTCCAGGATT CCCAGgtatt tgaagggatt tttgtggttt ccctttatat
taaactcctc tgggacaaga tagccatttt ctgtattgac tgggtaaagg ttgtagccct
gttgctttgc cataaaactg tatgtacctt ctgtgcagGC ATGAAAGGAC CCAGTGGAGT
ACCTGGATCA GCTGGCCCTG AGGGGGAACC GGgACTTATT GGTCCTCCAG gtaagactta
ttcctgaaga tagttatacc tgatacttag atgctttaaa gaatttgaaa gttttcattc
tgtctttcag ccagaccatc ggaggctaag t 7
tttggcttcc atttcttgta acctttctct ttccttcaa atttgtgtgt tttgtctcat
agGTCCTCCT GGATTACCTG GTCCTTCAGG ACAGAGTATC ATAATTAAAG GAGATGCTGG
TCCTCCAGGA ATCCCTGGCC AGCCTGGGCT AAAGGGTCTA CCAGGACCCC AAGGACCTCA
AGGCTTACCA Ggtaccaatg cagatcatct ttattatcat tattatactt ttaatttctg
ggatacatgt gcagaatgta caggtttgtt acataggtat 6
agaaccttat gtctcctaga tctgtccaga tgtgaaaata ttctactcat atttgaatgc
ctcattcttt tcctgtagGT CCAACTGGCC CTCCAGGAGA TCCTGGACGC AATGGACTCC
CTGGCTTTGA TGGTGCAGGA GGGCGCAAAG GAGACCCAGG TCTGCCAGGA CAGCCAGgta
agacaagtaa aacatgctgt tggtggaggg aaagtctttg agtctgagag acctctggac
atagggcctc cacttagagc tgtgagatct tctcttgatg ttagcatagc tgactggtga
atgtggac

Fig. 2C

5 aactaaggaa atatagtata tttattacct atgaaaggct ggcaagtttc cttgaaaggc
tgtttgctat tgttttagaa gaaaccaaag tatcattatc acgcagtcct ttactgtttt
ctctccaaat ctttctagGG ACGGCTGGCA GCTGCCTTCG TCGCTTTAGT ACCATGCCTT
TCATGTTCTG CAACATCAAT AATGTTTGCA ACTTTGCTTC AAGAAATGAC TATTCTTACT
GGCTCTCTAC CCCAGAGCCC ATGCCAATGA GCATGCAACC CCTAAAGGGC CAGAGCATCC
AGCCATTCAT TAGTCGgtaa ggcattgatt tagctgtgac ttttaccaat ccccagttag
ttagctagtc agatttgagt ccaaagctaa caatctgatg atattcctcc taggttaggt
agaacagagg tac

4 aactaaggaa atatagtata tttattacct atgaaaggct ggcaagtttc cttgaaaggc
tgtttgctat tgttttagaa gaaaccaaag tatcattatc acgcagtcct ttactgtttt
ctctccaaat ctttctagGG ACGGCTGGCA GCTGCCTTCG TCGCTTTAGT ACCATGCCTT
TCATGTTCTG CAACATCAAT AATGTTTGCA ACTTTGCTTC AAGAAATGAC TATTCTTACT
GGCTCTCTAC CCCAGAGCCC ATGCCAATGA GCATGCAACC CCTAAAGGGC CAGAGCATCC
AGCCATTCAT TAGTCGgtaa ggcattgatt tagctgtgac ttttaccaat ccccagttag
ttagctagtc agatttgagt ccaaagctaa caatctgatg atattcctcc taggttaggt
agaacagagg tac

3 aagtgcattt tttcacctttt tgtgatcatt gaaagagaca ttaatcggct tccatactaa
gaaggcttcc aatgaagcag gatggctact tctcacatgc tcactctgta gattatgttc
cttctccttt tcctttacca gATGTGCAGT ATGTGAAGCT CCAGCTGTTG TGATCGCAGT
TCACAGTCAG ACGATCCAGA TTCCCCATTG TCCTCAGGGA TGGGATTCTC TGTGGATTGG
TTATTCCTTC ATGATGgtat tttacactct tccttgcatt tgtcatcata gctgactgtc
cattccatct acatttcttc ccaatatgag gaatccctgt catttgcata ataagaagct

*Fig. 2D*

2 aagcttaaac ttcaaacagc ttctatccaa gcactgtgtt cccctcaca cattttttgt
aacatatttt cataatctgc ctattacttt ttttgacta cccttggtgt ggatactatt
gtcttacctc tgggcctgtt ccttcactag atttgaattt ggccaagctc agcacacatc
tttggatatt cactaagcta ttatggcaca tgggtattgc ggcacatttt tccttgtctt
ttatagCATA CAAGTGCAGG GGCAGAAGGC TCAGGTCAAG CCCTAGCCTC CCCTGGTTCC
TGCTTGGAAG AGTTTCGTTC AGCTCCCTTC ATCGAATGTC ATGGGAGGGG TACCTGTAAC
TACTATGCCA ACTCCTACAG CTTTTGGCTG GCAACTGTAG ATGTGTCAGA CATGTTCATg
taaagtgctt atagctttaa ttcaggtcca aagcttcctt cagagatgct agggaagaaa
gagacaattt atggatggtt tat

Fig. 2E 1
agaat cgttacaaaa tatctatgac cactaatggc tcttaaacca tactagtcac tgcattagat catattgctg aaaagtaaac cattaagtca ccaagagagc tacttaacac acaaaaaatg tttagttata aatttgaacc agtaacagaa tTgaaatacc agaaaatgtg gatctgattg tcttatttct tatttcccag

TAAACCTCAG TCAGAAACGC TGAAAGCAGG AGACTTGAGG ACACGAATTA GCCGATGTCA

AGTGTGCATG AAGAGGACAT AACATTTTGA AGAATTCCTT TTGTGTTTTA AAATGTGATA

TATATATATA TAAAATTCCT AGGATGCAGT GTCTCATTGT CCCCAACTTT ACTACTGCTG

CCGTCAATGG TGCTACTATA TATGATCAAG ATAACATGCT GACTAGTACC CATGAAGATT

CAGATGTACC TCAGCAATGC GCCAGAGCAA AGTCTCTATT ATTTTTCTAC TAAAGAAATA

AGGAAGTGAA TTTACTTTTT GGGTCCAGAA TGACTTTCTC CAAGAATTAT AAGATGAAAA

TTATATATTT TGCCCAGTTA CTAAAATGGT ACATTAAAAA TTCAATTAAG AGAAGAGTCA

CATTGAGTAA AATAAAAGAC TGCAGTTTGT GGGAAGAATT ATTTTTCACG GTGCTACTAA

TCCTGCTGTA TCCCGGGTTT TTAATATAAA GGTGTTAAGC TTATTTTGCT TTGTAAGTAA

AGAATGTGTA TATTGTGAAC AGCCTTTTAG CTCAAAATGT TGAGTCATTT ACATATGACA

TAGCATGAAT CACTCTTTAC AGAAAATGTA GGAAACCCTA GAATACAGAC AGCAATATTT

TATATTCATG TTTATCAAAG TGAGAGGACT TATATTCCTA CATCAAGTTA CTACTGAGAG

TAAATTTATT TTGAGTTTTA TCCCGTAAGT TCTGTTTTGA TTTTTTTTAA AAAACAAACC

CTTTTAGTCA CTTTAATCAG AATTTTAAAT GTTCATGTTA CATACCAAAT TATAATATCT

AATGGAGCAA TTTGTCTTTT GCTATATTCT CCAAGATTAT CTCTTAAGAC CATATGCCCC

CTGTTTTAAT GTTTCTTACA TCTTGTTTTT ACTCATTTCT GACTGGACAA AGTTCTTCCA

AACAATTCTG AGAAACAAAA ACACACACGC AGAATTAACA ATTCTTTTCC CTGTGCTTCT

TATGTAAGAA TCCTCCTGTG GCCTCTGCTT GTACAGAACT GGGAAACAAC ACTTGGTTAG

TTGTTATAAA TACTCACAGG ATACCTTATT TCCCTAGCTA TCATCTCCTG ACTTAATGIT

TTTTAAACCC ACCAATATAA ATTTAATTAA AGATATATGT Tgtaaggatg gtctgttgtg tatctcttca gcctgtgtgg aaaaaacccc tgctcattta cagatagatt accaatctgc acatcaacaa gtcatctctt cccagggaat cagtttctcc acgctttgat cactctgtta gtagatagaa aacatatagt aatgtaaact ttttccaatg aagaaaacta cctattggaa gacatttcca agataataaa ttcttgaca acattgtgtt aatggctaag aaaggaaaca actggcttct atttggggaa gaattc

Fig. 2F

|  |  |  | GENE | |
|---|---|---|---|---|
| GENE SEGMENT | | | α5(IV) | α1(IV)[a] |
| EXON | 19 | (34) | 150 | 153 |
| INTRON | 18 | (34) | 1500 | 161 |
| EXON | 18 | (35) | 99 | 99 |
| INTRON | 17 | (35) | 1450 | 115 |
| EXON | 17 | (36) | 90 | 90 |
| INTRON | 16 | (36) | 300 | 1100 |
| EXON | 16 | (37) | 140 | 140 |
| INTRON | 15 | (37) | >5000 | 300 |
| EXON | 15 | (38) | 127 | 127 |
| INTRON | 14 | (38) | >4500 | 97 |
| EXON | 14 | (39) | 81 | 81 |
| INTRON | 13 | (39) | 1210 | 600 |
| EXON | 13 | (40) | 99 | 99 |
| INTRON | 12 | (40) | 560 | 1500 |
| EXON | 12 | (41) | 51 | 51 |
| INTRON | 11 | (41) | 940 | 2000 |
| EXON | 11 | (42) | 186 | 186 |
| INTRON | 10 | (42) | 7000 | 800 |
| EXON | 10 | (43) | 134 | 134 |
| INTRON | 9 | (43) | 3100 | 2670 |
| EXON | 9 | (44) | 73 | 73 |
| INTRON | 8 | (44) | 133[d] | 960 |
| EXON | 8 | (45) | 72 | 72 |
| INTRON | 7 | (45) | 870 | 1390 |
| EXON | 7 | (46) | 129 | 129 |
| INTRON | 6 | (46) | 4480 | 1510 |
| EXON | 6 | (47) | 99 | 99 |
| INTRON | 5 | (47) | 1400 | 1210 |
| EXON | 5 | (48) | 213 | 213 |
| INTRON | 4 | (48) | 5000 | 960 |
| EXON | 4 | (49) | 178 | 178 |
| INTRON | 3 | (49) | 2050 | >13000 |
| EXON | 3 | (50) | 115 | 115 |
| INTRON | 2 | (50) | 345[d] | 2900 |
| EXON | 2 | (51) | 173 | 173 |
| INTRON | 1 | (51) | 900 | 1900 |
| EXON | 1[b] | (52)[c] | 1245 | 1383 | a) Soininen et al., J. Biol. Chem. 264, 13565-13571, 1989
b) The number as counted from the 3' end
c) The number in parenthesis refers to the actual number in the previously determined human α1(IV) gene as counted from the 5' end
d) sequenced (Zhou et al., 1991a, Genomics, in press)

Fig. 3

METHOD FOR DETERMINING THE NUCLEOTIDE SEQUENCE OF THE GENE FOR THE α5(IV) CHAIN OF HUMAN TYPE IV COLLAGEN

This is a continuation of application Ser. No. 08/346,336 filed on Nov. 29, 1994, now abandoned which is a continuation of application Ser. No. 07/635,475 filed on Dec. 28, 1990, now abandoned, which is a continuation-in-part patent application to the parent U.S. application "Method for determining the nucleotide sequence of a novel α5(IV) chain of human type IV collagen" Ser. No.07/377,238, filed on Jul. 7, 1989 and issued on May 19, 1992 as U.S. Pat. No. 5,114,840.

FIELD OF THE INVENTION

The present invention relates to a method for isolating and Identifying the nucleotide sequence of the human gene for the type IV collagen a5(IV) chain. The present invention is directed to the determination of the nucleotide sequence of the gene for the a5(IV) collagen chain in individuals by any method known to the art e.g. cloning from genomic DNA libraries or amplifying gene regions with the polymerase chain reaction (PCR) and studying their physical properties or nucleotide sequences. In addition, the invention is directed to the use of the nucleotide sequences of the a5(IV) gene to amplify or identify the nucleotide sequences of the a5(IV) gene.

BACKGROUND OF THE INVENTION

Basement membranes (BM) are special extracellular, sheet-like structures that separate cells of organs from the underlying connective tissues. They form flexible boundaries that provide physical support and biological signals required for maintainance of morphology and orderly development of distinct tissue patterns. The BM protein components can have different subunits and molecular compositions that possess the necessary functional elements for the tissues concerned. This has become more apparent as new chains with restricted tissue distributions have been found e.g. for type IV collagen and laminin. The basement membranes have also an Important role in the correct regeneration of tissues following injuries such as during post-wound reformation of skin and nerves. Basement membranes also function as macromolecular filters e.g. in kidneys where the glomerular basement membrane is the sole filtration barrier between the capillary lumen and the urinary space, hindering the blood to urine leakage of macromolecules and blood cells.

Basement membranes are composed of several specific components that include type IV collagen, laminin, entactin (nidogen) and proteoglycans. Type IV collagen is the major structural component of basement membranes and it forms the framework of these extracellular structures. In addition, basement membranes contain SPARK (BM-40), fibronectin and type VII collagen that are also present in other extracellular structures. The exact molecular compositions of basement membranes in different tissues Is not well known but there Is growing evidence that even the ubiquitous basement membrane components as type IV collagen and laminin have different chain compositions in different tissues. Additionally, there are some proteins such as pemphigoid antigen that are present only In the basement membranes of skin.

Type IV collagen is the major structural component of basement membranes and It can provide up to 60 % of the structure. As all collagens, the type IV collagen molecule is formed by three a chains coiled around each other to form the collagen triple helix with the repeated Gly-X-Y-triplet amino acid sequence containing regions. The molecule has a triple-helical 400 nm-long collagenous part and a C-terminal globule with a diameter of about 15 nm. The collagenous domain sequence has several interruptions in the otherwise continuous collagenous Gly-X-Y repeat sequence that give flexibility to the type IV collagen molecules as opposed to the rigid rod-like molecules of fibrillar collagens with uninterrupted helices. The triple-helical type IV collagen molecules can form dimers by the attachment of two NC domains and tetramers by the 30 nm overlapping cross-linking of four molecules of their amino terminal ends (Timpl, Eur. J. Biochem. 180: 487–502, 1989).

The major form of the molecules consists of two α1(IV) and one α2(IV) chain. The applicants have determined the entire amino acid sequence of these two chains from man by cloning and sequencing cDNA clones covering the coding region (Soininen et al., FEBS. Lett., 225: 188–194, 1987; Hostikka and Tryggvason, J. Biol. Chem., 263: 19488–19493, 1988). The results showed that the α1(IV) chain is synthesized as a 1969 amino acid residue polypeptide as compared to 1712 residues in the α2(IV) chain. The carboxyl terminal NC domains of the two chains are very similar with 63 % identical amino acid residues. The sequence identity of the two chains is much less conserved in the triple-helical region with only 49 % identity; where only 22 % of the X and Y residues in the collagenous Gly-X-Y-repeat sequence are conserved. Two other distinct type IV collagen α chains, referred to as α3(IV) and α4(IV), have been described (Butkowski et al., J. Biol. Chem., 262: 7874–7877, 1987; Saus et al. J. Biol. Chem. 263: 13374–13380, 1988; Gunwar et al., J. Biol. Chem., 265: 5466–5469, 1990).

Of importance with respect to the present invention is our recent discovery of yet another novel human type IV collagen α5(IV) chain by cDNA cloning (Hostikka et al., Proc. Natl. Acad. Sci. USA. 87: 1606–1610, 1990 and the parent U.S. patent application "Method for determining the nucleotide sequence of a novel α5(IV) chain of human type IV collagen" Ser. No. 377,238, filed on Jul.7, 1989 now U.S. Pat. No. 5,114,840. Amino acid sequence comparison with the α1(IV) and α2(IV) chains and the data available of the α3(IV) and α4(IV) chains demonstrated that the α5(IV) chain is a distinct gene product which is closely related to the α1(IV) chain. In the NC domain the identity between the deduced amino acid sequences is 83 % with the α1(IV) chain and with α2(IV) chain 63 %; whereas in the collagenous domain the identities are 58 % and 46 %, respectively. Furthermore, all the interruptions in the collagenous Gly-X-Y-repeat sequence of the α5(IV) chain coincide with those in the α1(IV) chain but only partially with those In the α2(IV) chain (Hostikka et al., Proc. Natl. Acad. Sci. USA. 87: 1606–1610, 1990 and the parent U.S. patent application "Method for determining the nucleotide sequence of a novel α5(IV) chain of human type IV collagen" Ser. No. 377,238, filed on Jul. 7, 1989, now U.S. Pat. No. 5,144,840.

With α5(IV)-specific peptide-antibodies, the chain was shown to be almost exclusively present in the GBM in the kidney (Hostikka et al., Proc. Natl. Acad. Sci. USA. 87: 1606–1610, 1990 and the parent U.S. patent application "Method for determining the nucleotide sequence of a novel α5(IV) chain of human type IV collagen"Ser. No. 377,238, filed on Jul.7, 1989, now U.S. Pat. No. 5,144,840 and the continuation-in-part application "Immunological methods for the detection of the human type IV collagen α5 chain", filed Dec. 20, 1990, U.S. application Ser. No. 630,563 whereas the well characterized α1(IV) and α2(IV) chain are believed to be ubiquitous basement membrane (BM) components present in all BMs.

Using cDNA probes and both somatic cell-hybrids and in situ hybridization, the gene for the human type IV collagen α5 chain COL4A5 was localized to the q22 region on the long arm of chromosome X (Hostikka et al., Proc. Natl. Acad. Sci. USA. 87: 1606–1610, 1990 and the parent U.S. patent application "A Method for determining the nucleotide sequence of a novel α5(IV) chain of human type IV collagen" serial number 377,238, filed on Jul. 7, 1989, U.S. Pat. No. 5,144,840. This is different from the human genes COL4A1 and COL4A2 coding for the α1(IV) and α2(IV) chains that both are located on the terminal end of the long arm of the chromosome 13 (Boyd et al., Hum. Genet., 74: 121–125, 1986; Griffin et al., Proc. Natl. Acad. Sci. USA., 84: 512–516, 1987). The α1(IV) and α2(IV) chains are transcribed by different DNA strands from a common bidirectional promoter in opposite directions, so that the transcription initiation sites are separated by only 42–127 bp (P öschl et al., EMBO J., 7: 2687–2695, 1988; Soininen et al., J. Biol. Chem., 263: 17217–17220, 1988).

The applicants have determined the complete structure of the human α1(IV) gene (Soininen et al., J. Biol. Chem.,264: 13565–13571, 1989) and the partial structure for the human α2(IV) gene (Hostikka and Tryggvason, FEBS Lett., 224: 297–305). The α1(IV) gene contains 52 exons spread over at least 100 kb of genomic DNA. The sizes of translated exons vary from 27 to 213 bp. The collagenous domain is encoded by 47 exons with sizes varying between 27 and 192 bp. About half of them begin with complete codons whereas the other half of the gene has mainly split codons, usually beginning with the second base for glycine, but also two exons begin with the third base of a codon. Thus, the exon size pattern of this gene is very different from the highly conserved structure of the genes for the fibrillar collagens. The largest exon coding for a translated sequence is the junction exon coding for the carboxyl-terminal part of the collagenous domain and the amino-terminal part of the NC domain. Four more exons code for the NC domain, the last of them containing the 3 untranslated region (Soininen et al., J. Biol. Chem., 264: 13565–13571, 1989).

The region characterized from the human α2(IV) gene shows a different pattern. The NC domain is encoded by three exons as compared to five in the α1(IV) gene. The similarity of the two genes is demonstrated by the fact that although the exon sizes differ, the locations of the introns are exactly the same when comparing to the aligned amino acid sequences of the chains. On the other hand, the exons in the collagenous domain coding region of the α2(IV) gene are different so that only one intron location seems to coincide, whereas all the exon sizes differ nor do they obey the fibrillar 54 bp pattern.

The exons in the collagenous region coding part begin with split glycine codons (Hostikka and Tryggvason, FEBS Lett., 224: 297–305).

Due to the wide distribution of basement membranes in the body, they are frequently affected in local and systemic diseases, and in many instances the consequent pathological changes lead to severe clinical complications. These diseases may be acquired i.e. complications of a disease that do not primarily involve basement membrane, or they can be genetically determined inherited diseases that are due to gene mutations leading to abnormal structure and function of the basement membrane. The best known example of an acquired disease is diabetes mellitus where the basement membrane structure is affected in almost all tissues in the body, resulting in dysfunction of small blood vessels (microangiopathy), kidneys (nephropathy), and nerves (neuropathy). The biochemical alterations leading to these malfunctions are still poorly understood. Also, autoimmune diseases, such as Goodpasture syndrome, affect the basement membranes. The antibody binds to the glomerular basement membrane and triggers its destruction by complement binding and phagocytosis.

Examples of inherited diseases are: (1) the congenital nephrotic syndrome that is characterized by extensive leakage of blood proteins through the renal glomerular basement membrane into the urine (proteinuria); and (2) the Alport syndrome where malfunction of the glomerular basement membrane leads to the passage of blood cells into urine (hematuria), eye lesions and hearing loss. The actual gene defect leading to the congenital nephrotic syndrome is yet completely unknown. The Alport syndrome is primarily an X-linked inherited kidney disease that has been linked by chromosomal markers to chromosome X region q22–26 (Atkin et al., Am. J. Hum. Genet., 42: 249–255, 188; Flinter et al., Genomics 4: 335–338, 1989) It leads to malfunction of kidneys and it can be treated only by dialysis or renal transplantation. The disease has been shown to be associated with progressive ultrastructural abnormalities, such as patchy thickening and thinning of the glomerular basement membrane and splitting of the lamina densa. These results and the more recent immunological studies have suggested that the cause of the Alport syndrome would be an abnormal or absent type IV collagen α chain (Spear, Clin. Nephrol. 1: 336–337, 1973; Kashtan et al., J. Clin. Invest., 78: 1035–1044, 1986).

Of importance with respect to the present invention is our recent discovery that a mutation in the type IV collagen α5(IV) gene, that changes the structure of the produced polypeptide chain, causes Alport syndrome. Eighteen Alport kindreds were studied and in three of them an abnormal fragment pattern was shown with restriction fragment length polymorphism (RFLP) analysis for the α5(IV) gene (Barker et al., Science 248: 1224–1227, 1990; and the U.S. patent application "Method for detection of Alport syndrome", Ser. No. 07/534,786, filed on Jun. 7, 1990 now abandoned, and the parent U.S. patent application "Method for determining the nucleotide sequence of a novel α5(IV) chain of human type IV collagen" Ser. No.377,238, filed on Jul.7, 1989, now U.S. Pat. No. 5,144,840. In kindred EP, there was a deletion of about 15 kb of the gene, containing exons 5 through 10 as counted from the 3' end. In kindred P, there was a point mutation that changed a codon for a conserved cysteine residue to a codon for serine and created restriction sites for PsiI and BglI restriction endonucleases (Barker et al., Science 248: 1224–1227, 1990; the U.S. patent application "Method for detection of Alport syndrome", Ser. No. 07/534,786, filed on Jun. 7, 1990 now abandoned, and the parent U.S. patent application "A Method for determining the nucleotide sequence of a novel α5(IV) chain of human type IV collagen" Ser. No. 377,238, filed on Jul.7, 1989 now U.S. Pat. No. 5,144,840 and Zhou, et al., 1991a, Genomics, in press). Later studies have shown that in about 10 % of the Alport patients, a gene rearrangement can be observed with the α5(IV) cDNA clones in RFLP analysis.

SUMMARY OF THE INVENTION

The present invention provides for a method for isolation and partially characterizing the nucleotide sequence of the gene coding for the human type IV collagen α5(IV) chain.

The invention provides for the use of the identified nucleotide sequence (or DNA fragments thereof) to detect mutation(s) in Individual genes specific for the α5(IV) chain which can, directly or indirectly, produce human diseases. The invention relates to the use of noncoding intervening sequences (introns) between and flanking the α5(IV) polypeptide chain coding regions (exons) of the α5(IV) gene to amplify and determine the physical properties and nucleotide sequence of the said gene for both protein coding regions and noncoding regions. Also, the Invention relates to the use of gene fragments generated through amplification from human genomic or cloned DNA for the detection and analysis of the gene, such as in detection of mutations. Additionally, the invention provides for the use of the Identified recombinant DNA cloning vectors and transformed hosts which contain a vector which has a fragment of the α5(iV) gene inserted into.

The invention further related to the detection of variations of an individual's COL4A5 gene in comparison with the known normal COL4A5 gene. In one embodiment this is done by RFLP analysis, wherein an individual's genomic DNA is cut by restriction enzyme, size-fractionated and tested for the sizes of DNA fragments of the α5(IV) gene. The invention relates to nucleotide sequences flanking the polypeptide chain coding region (intron sequences) that can be used to amplify coding regions (exons) with the flanking consensus sequences needed for the proper splicing of the pre-mRNA to mRNA by cloning or the method of polymerase chain reaction (PCR) or any other method known to the art; and to determining the differences of those sequences with the normal COL4A5 gene by various techniques, such as single-strand conformation polymorphism analysis, denaturing gradient gel electrophoresis, S1 nuclease mapping nucleotide sequencing or any other method known to the art.

Finally, the invention related to the fragments of the normal human α5(IV) gene that may by used to correct a defective gene by gene therapy.

DESCRIPTION OF THE DRAWINGS

The following is a description of the drawings which are presented for the purpose of illustrating the invention and not for the purpose of limiting same.

FIG. 2 shows the nucleotide sequence of the 19 most 3' exons of the α5(IV) gene and flanking regions. Exon sequences (SEQ ID NO: 1 through SEQ ID NO: 19 ) are shown in capital letters and Intron sequences in lower case letters. The exons are numbered from the 3' end.

FIG. 3 is a table where the sizes of the exons and introns of the α5(IV) gene Is compared with those of the α1(IV) gene. The exon sizes differ only once, in exon 19 (SEQ ID NO: 19) where one amino acid residue is missing from the α5(IV) chain when comparing the aligned amino acid sequences with those of the α1(IV) chain. On the other hand, the introns show no similarity in their size pattern.

DETAILED DESCRIPTION OF THE INVENTION

Figure 1:
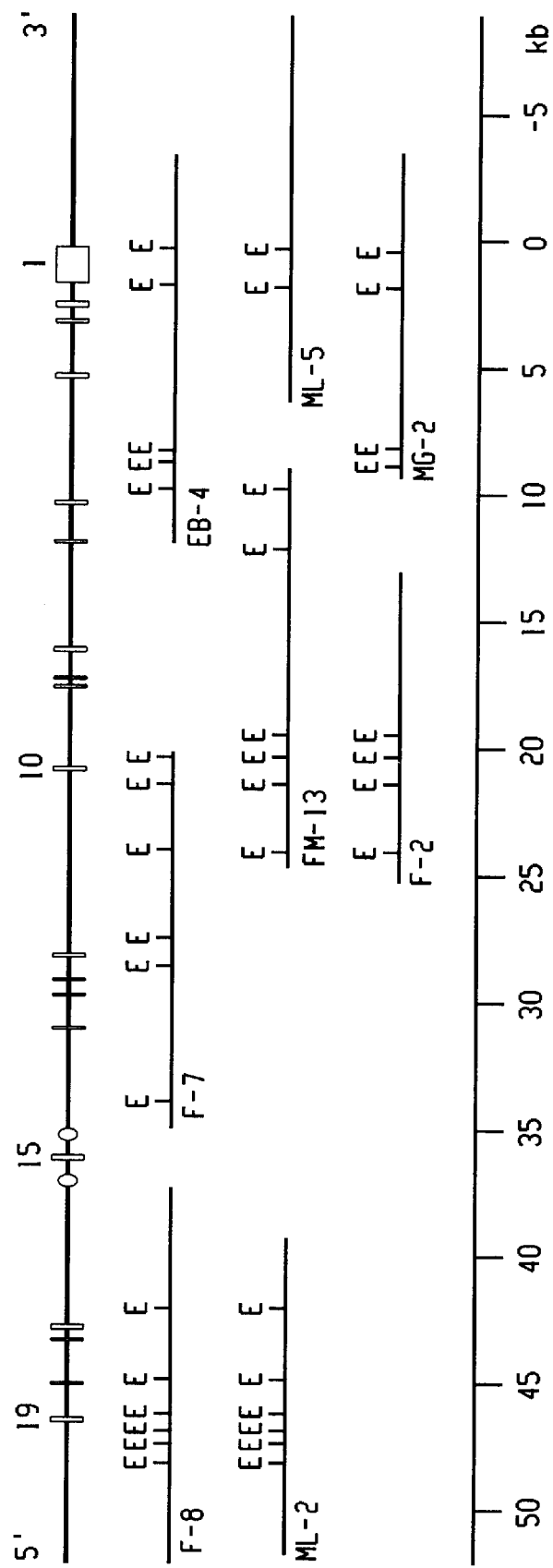
FIG. 1 is a restriction map of eight cloned fragments of the α5(iV) gene. A scale demonstrating the size differences in kilo base pairs is shown below the cloned gene fragments (in the middle). The EcoRI restriction sites (E) and the aligned positions of the eigth λ clones are shown. On top is a diagram of the gene with α5(IV) polypeptide chain coding regions (exons) indicated by shadowed boxes and noncoding regions (introns and the 3' flanking region) indicated by a solid line. The exons are numbered from the 3'end of the gene.
Figure 4:
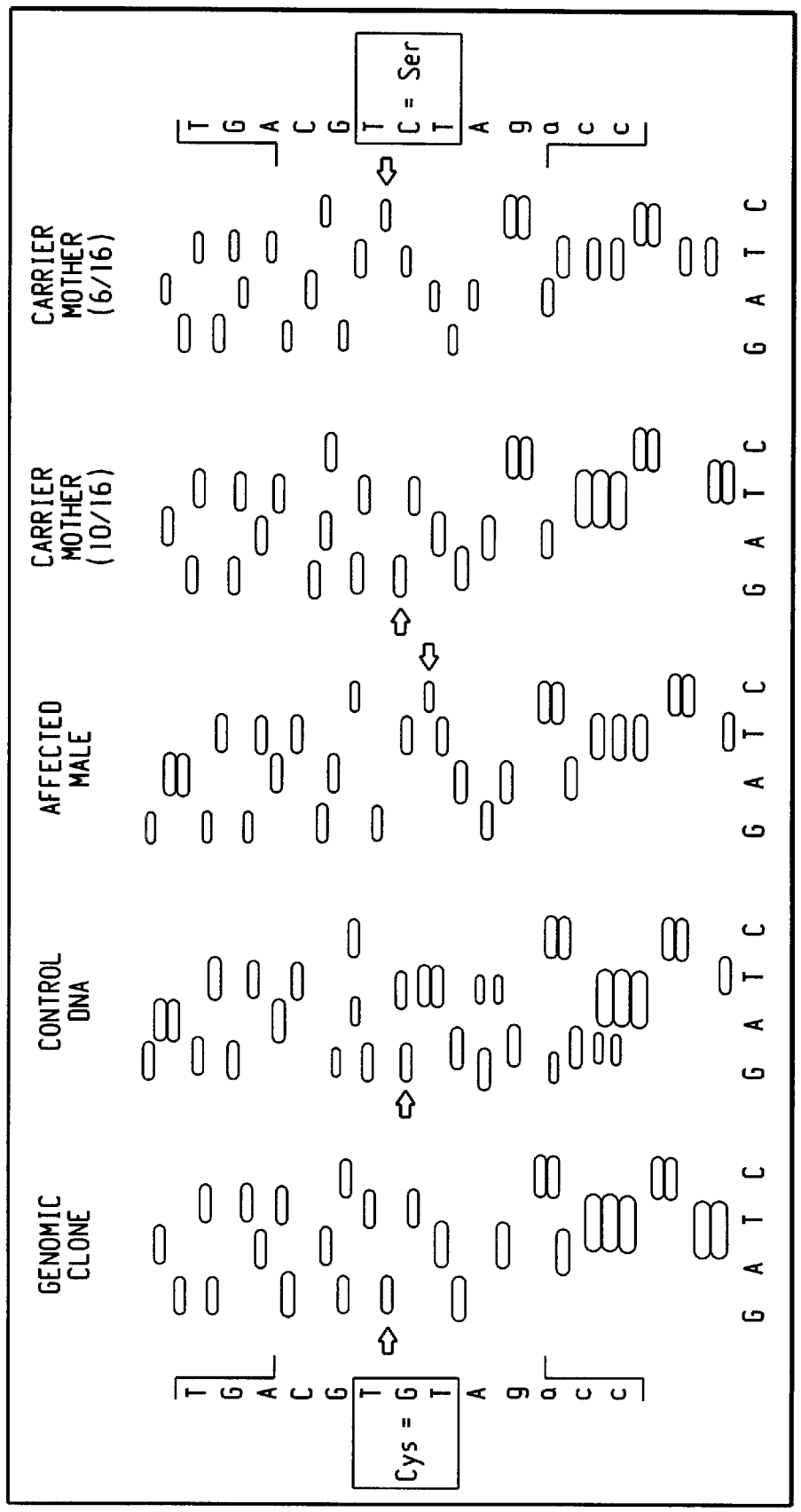
FIG. 4 shows partial sequence of a PCR-amplified segment of the α5(IV) gene from normal individuals and individuals carrying a mutated gene. The amplified fragments were cloned into an M13 vector and sequenced with the dideoxynucleotide chain termination method. The sequencing reaction samples were electrophoresed on a polyacrylamide gel followed by autoradiography. The results show sequence differences between normal and mutated DNA.

The applicants have isolated and characterized fragments of the gene for the human type IV collagen α5(IV) chain and determined the structure and partial sequence (SEQ ID NO: 1–SEQ ID NO: 19) for the gene. The gene clones in x phage were screened with the cDNA clones coding for the human α5(IV) chain (Hostikka et al., Proc. Natl. Acad. Sci. USA. 87: 1606–1610, 1990 and the parent U.S. patent application "A Method for determining the nucleotide sequence of a novel α5(IV) chain of human type IV collagen" serial number 377,238, filed on Jul. 7, 1989, now U.S. Pat. No. 5,114,840). The genomic clones obtained, cover approximately 50 kb or about half of the COL4A5 gene in eight overlapping clones (Zhou, et al., (1991), Genomics, Vol. 9(1) 10–18 Map of the clones with respect to each other and the encoded exons with the restriction sites for EcoR1 are shown in FIG. 1.

Fragments of the genomic clones for the COL4A5 gene that hybridized with the cDNA clones and therefore contained coding regions, were subcloned Into M13 and/or pUC-vectors for sequencing and further restriction mapping. The coding nucleotide sequence of the cDNAs was used to make oligonucleolide primers for sequencing the exons and their flanking regions from the genomic clones; By the sequence identity of the α5(IV) chain with the α1 (IV) chain, it was anticipated that the exon-intron boundaries would coincide, as compared to the aligned amino acid sequences. This was shown to be the case, as shown in FIG. 3. Six overlapping genomic clones (ML-5, MG-2, EB-4, FM-13, F-2 and F-7) cover about 9.5 kb of the 3flanking region and about 36 kb of the gene, including 14 most 3 exons. Two additional clones (F-8 and ML-2) that do not overlap the previous clones, contain exons 16 through 19(SEQ ID NO: 16–SEQ ID NO: 15) Exon 15 was shown to be one exon and sequenced by amplifying the coding region with PCR reaction, using cDNA derived primers. The exons 1–5(SEQ ID NO: 1–SEQ ID NO: 5) code for the NC domain. Exon 5(SEQ ID NO: 5) is a Junction exon that contains 142 bp coding for the NC domain and 71 bp coding for the collagenous region. Exons 6–19(SEQ ID NO: 6–SEQ ID NO: 19)code for collagenous Gly-X-Y-repeat sequence and have sizes differing between 51 and 186 bp. The exons and their flanking Intron sequences are shown In the FIG. 2. The intron sizes analyzed very between 133 and 7000 bp and show no correlation with the sizes of the corresponding introns in the α1(IV) gene.

EXAMPLES

EXAMPLE 1

Isolation and characterization of the gene clones for the human α5(IV) gene.

Human genomic libraries in λ Charon 4A, in λ EMBL-3 or λ Fix, made from genomic DNA isolated from human lymphocytes, were screened with the cDNA clones coding for the human α5(IV) chain (Hostikka et al., Proc. Natl. Acad. Sci. USA. 87: 1606–1610, 1990 and the parent U.S. patent application "Method for determining the nucleotide sequence of a novel α5(IV) chain of human type IV collagen" serial number 377,238, filed on Jul.7, 1989, now U.S. Pat. No. 5,114,840). For each plate, a sample of 30,000 plaque forming units of a library was infected to 300 µl *E. coli LE* 392 plating bacteria (in 20 mM MgSO$_4$) at 37° C. for 20 minutes and plated in 7 ml top-agar (1 % tryptone, 0.8 % NaCl, 1.4 % LMP-agar) on agar plates containing 1 % tryptone, 0.5 % yeast extract, 0.5 % NaCl and 100 µg/ml ampicillin. The λ phage were grown at 37° C. overnight. Duplicate nitrocelluloce filters were made by allowing them to stand on the plate for 1 and 2 minutes following 5 minutes denaturation in 0.5 M NaOH, 1.5 M NaCI; neutralizing In 1 M Tris (Tris[hydroxymethyl]aminomethane), pH 8.0, 1.5 M NaCI for 5 minutes and balancing to 2xSSC (IxSSC Is 0.15 M NaCI, 0.015 M sodium citrate, pH 7.0) before air drying and baking at 80° C. for 2 h.

For hybridization, the nitrocellulose filters were balanced in 5xSSC. Nick translation labeling of the cDNA inserts with deoxycytidine 5'-[α-$^{32}$P]triphosphate (Amersham, PB 10205) was carried out with a Promega kit according to the manufacturer's instructions. The filters were prehybridized for 2 h and hybridized with the labeled cDNA probes overnight at 65° C. in 5xSSC, 5xDenhardt's solution, 0.1 % SDS, 50 µg/ml denatured salmon sperm DNA (50xDenhardt's solution is 1 % Ficoll, 1 % polyvinylpyrrolidone, 1% BSA). The nitrocellulose filters were washed first in 2xSSC, 0.1 % SDS at RT and then at 65° C. with several changes and washing solution up to 0.2xSSC, 0.1 % SDS. Autoradiography was done at –70° C. overnight. Clones showing duplicate positive signals for the cDNA clones were picked and rescreened until pure plaques were isolated. Phage were grown in larger amounts and isolated as pure λ-DNA with a rapid method containing DNAse I and RNAse A treatment of the lyzed growing medium, PEG precipitation, proteinase K treatment, phenol and chloroform extractions and ethanol precipitations. λ-DNA of the clones was digested with different restriction endonucleases and electrophoresed In 1 % agarose gel containing ethidium bromide to separate the genomic Inserts from the λ-vector and to determine the sizes of gene fragments in order to make a restriction map of the gene. DNA was transferred from the gel to a nitrocellulose filter by Southern blotting and hybridized with the cDNA mixture. The genomic fragments that hybridized with the cDNA clones were isolated and subcloned Into M13 or pUC vectors for sequencing and further restriction mapping. The clones and a partial restriction map is shown in FIG. 1.

For the detection of a gene fragment containing a certain exon, the Southern filter could be hybridized with an oligonucleotide probe. Knowing the exon present In a fragment, the exon could be sequenced using the same oligonucleotide as a primer for sequencing. For oligonucleotide hybridization, the nitrocellulose filter was prewashed in 3xSSC, 0.1 % SDS at 65° C. overnigth, prehybridized In 6xSSC, 5xDenhardt's , 0.5 % SDS, 100 µg/ml denatured salmon sperm DNA, 0.05 % Na-pyrophosphate for 2 h at 37° C. and hybridized with labeled oligonucleotide mixture in 6xSSC, 5xDenhardt's solution, 250 µg/ml denatured salmon sperm DNA, 0.05 % Na-pyrophosphate overnight at 37° C. For making the oligonucleotide probe, 500 ng of the oligonucleotide was labeled with too µCi adenosine 5'[Υ-$^{32}$P] triphosphate (in 10 µl; Amersham, PB 10168) in 20 mM MgCl$_2$, 200 mM Tris, pH 7.6, 40 mM β-mercaptoethanol with IU T4-polynucleotide kinase in 40 µl reaction mixture at 37° C. for 1 hour. After the hybridization, the nitrocellulose filter was washed with 6xSSC, 0.05 % Na-pyrophosphate once at room temperature, twice 10 min. at 37° C. and at least twice 10 min. at 42° C. Autoradiography was performed at –70° C. for two days (DuPont Cronex).

EXAMPLE 2

Determining the nucleotide sequencing of the exons and flanking intron sequences The genomic fragments containing coding regions of the α5(IV) gene were subcloned into M13 or pUC vectors for sequencing. Nucleotide sequencing was done with the Sanger dideoxy nucleotide sequencing method using Sequenase (United States Biochemical Corporation) and deoxyadenosine 5'-(α-[$^{35}$S]thio)triphosphate (Ahersham, SJ1304) according to manufacturer's instructions. Both "universal primer" and sequence specific oligonucleotides were used as primers. The sequences were determined from both strands, yielding the entire sequence of each exon together with sequences of the adjacent intervening regions (introns). The sequences of exons 1–14 (SEQ ID NO: 1–SEQ ID NO: 14) and 16–19 (SEQ ID NO: 16–SEQ ID NO: 19) together with varying length of intron sequences are shown in FIG. 2. The sequence of exon 15 (SEQ ID NO: 5) was determined after amplification from genomic DNA by PCR reaction (see example 3.) using cDNA derived primers with flanking restriction sites. The PCR product was purified, linker sequences were digested to produce cohesive cloning sites and the fragment was subcloned into M 13-vectors for sequencing.

EXAMPLE 3

Polymerase chain reaction amplification of fragments of the α5(IV) gene

For the amplification of exon 15 (SEQ ID NO: 15) oligonucleotide primers P1 (5'-CTAGAATTCG-CGTGAGCCTTGGTCTGCCT-3')(SEQ ID NO: 20) and P2 (5 '-CCGMGCTTCTGGGMTCCAGGAAGGC-3 ')(SEQ ID NO: 21) were designed to contain EcoRI and Hindill restriction sites, respectively. The reaction was performed with a Perkin-Elmer/Cetus PCR kit using 1 µg of human lymphocyte DNA as template and 25 pmol of primers according to manufacturer's recommendations. The DNA was denatured at 94° C. for 10 minutes and cooling on ice for 3 minutes. After the addition of Taq polymerase, 25 cycles (denaturing at 94° C. for 1.5 minutes, annealing at 55° C. for 2 minutes, and extension at 72° C. for 2 minutes) were carried out. The amplified product was extracted with phenol/chlorophorm, digested with EcoRI and HindIII endonucleases, and electrophoresed in NuSieve GTG low-melting-point agarose (FMC BioProducts) gel. A DNA fragment of about expected size (145 bp) was excised from the gel and subcloned into M13 vectors for sequencing.

For the comparison of normal and altered gene sequences, a 1038 bp fragment containing the exons 2 and 3(SEQ ID NO: 2 and SEQ ID NO: 3) was amplified. Oligonucleotide primers P3 (5'-GACTCTAGAAAGGCCA TTGCACTGGTT-3')(SEQ ID NO:22) upstream (to the 5') from exon 3 (SEQ ID NO: 3 ) and P4. (5'-AGCGAATTCCTGACCTGAGTCATGTAT-3')(SEQ ID NO:23) to the downstream (3') from exon 2(SEQ ID NO: 2), with XbaI and EcoRI restriction sites, respectively. The PCR reaction of 35 cycles (denaturing at 94° C. for 1.5 minutes, annealing at 65° C. for 2 minutes, and extension at 72° C. for 2 minutes), subcloning and sequencing were carried out as above. The sequence of the exon 3 (SEQ ID NO: 3 ) showed a difference in a DNA sample from an Alport patient compared to normal individual's gene and an isolated genomic clone.

EXAMPLE 4

Denaturing gradient gel electrophoresis of PCR-amplified α5(IV) gene regions.

The amplified gene fragments can be separated according to their physical properties showing base differences between samples. The amplified fragments of different individuals were seperated according to melting temperatures In denaturing gradient gel electrophoresis (DGGE). The denaturing gradient gel electrophoresis was performed in 10 % polyacrylamide gels with a linerarly gradient from 40 % denaturant to 75 % denaturant (100% denaturant is 7M urea, 40% (vol/vol) formamide) at 150 V for 5 hours or 80 V overnight. The gel was stained with ethidium bromide solution destained with water and photographed.

What is claimed is:

1. A process for isolating and identifying genomic DNA clones which code for a portion of the α5 (IV) gene of human type IV collagen, said portions comprising gene fragments as set forth in SEQ ID NOs: 1–19, wherein the process comprises the steps of:
   a) labeling a nucleic acid selected from the group consisting of SEQ ID NOS: 1–19 or cDNAs corresponding thereto with a detectable label;
   b) screening a genomic library with the labeled nucleic acids obtained in step a) in order to isolate those genomic clones containing coding regions of the human type IV collagen α5 (IV) chain comprising gene fragments as set forth in SEQ ID NOs: 1–19;
   c) isolating the genomic clones obtained in step b) that contain coding regions of the gene for the human type IV collagen α5 (IV) chain;
   d) cloning the isolated genomic clones of step c) into a vector and inserting the vector into a bacterial or other host; and,
   e) sequencing said genomic clones of steps d) thereby identifying the isolated genomic DNA clones comprising SEQ ID NOs: 1–19.

2. The process of claim 1, wherein the genomic library comprises a human lymphocyte genomic library.

3. An isolated gene fragment consisting of any one of the sequences set forth in SEQ ID NOs: 1–19.

4. A process for identifying differences in the nucleotide sequence of a portion of the gene coding for α5 (IV) polypeptide chain of human type IV collagen comprising the steps of:
   a) labeling a nucleic acid selected from the groups consisting of SEQ ID NOs: 1–19 or cDNAs corresponding thereto with a detectable label;
   b) screening a genomic library with the labeled nucleic acids obtained in step a) in order to isolate those genomic clones containing coding regions of the portion of the human type IV collagen α5 (IV) chain;
   c) isolating the genomic clones obtained in step b) that contain coding regions of the portion of the gene for the human type IV collagen α5 (IV) chain;
   d) cloning the isolated genomic clones of step c) into a vector and inserting the vector into a bacterial or other host;
   e) sequencing said genomic clones of step d);
   f) identifying coding (EXON), intervening (intron) and flanking sequences of the portion of the gene for the human α5 (IV) type IV collagen chain; and,
   g) identifying differences between the portions of the genes for the human α5 (IV) type IV collagen chain independently obtained by the process comprising steps a)–f) above by comparing said sequences.

5. A method for identifying the size of a restriction fragment of the portion of the human type IV collagen α5 chain (COL4A5) gene which comprises:
   a) contacting separated restriction fragments obtained from a restriction enzyme digest of DNA of an individual with one or more detectable probes consisting of SEQ ID NO: 1–19 or cDNAs corresponding thereto.
   b) comparing the restriction fragment pattern so produced with a restriction fragment pattern obtained from an identical restriction enzyme digest of DNA from another individual;
   c) identifying the variation in fragment sizes between individuals.

* * * * *

```
                              SEQUENCE LISTING (1) GENERAL INFORMATION:

(iii) NUMBER OF SEQUENCES:      23

(2) INFORMATION FOR SEQ ID NO:1:

(i) SEQUENCE CHARACTERISTICS:
           (A) LENGTH:              1731 base pairs
           (B) TYPE:                Nucleic acid
           (C) STRANDEDNESS:        Single
           (D) TOPOLOGY:            Linear (ii) MOLECULE TYPE:            Nucleotide-genomic DNA (iii) HYPOTHETICAL:             Not relevant (iv) ANTI-SENSE:               Not relevant (v) FRAGMENT TYPE:            Eco RI restriction
              fragments (vi) ORIGINAL SOURCE:
           (A) ORGANISM:            Human
           (B) STRAIN:              Not relevant
           (C) INDIVIDUAL ISOLATE:  Not relevant
           (D) DEVELOPMENTAL STAGE: Not relevant
           (E) HAPLOTYPE:           Not relevant
           (F) TISSUE TYPE:         Liver
           (G) CELL TYPE:           Not relevant
           (H) CELL LINE:           Not relevant
           (I) ORGANELLE:           Not relevant (vii) IMMEDIATE SOURCE:
           (A) LIBRARY:   Human genomic library in lambda
               Charon 4A
           (B) CLONE:     M1-5, MG-2

(viii) POSITION IN GENOME:
           (A) CHROMOSOME/SEGMENT:       X
           (B) MAP POSITION:       q22
           (C) UNITS:              Not relevant (ix) FEATURE:
           (A) NAME/KEY:    COL4A5 collagen gene
           (B) LOCATION: Exxon 1 region from 3' end of gene
           (C) IDENTIFICATION METHOD:    DNA sequencing
           (D) OTHER INFORMATION:  The sequence contains 205
               nucleotides from intron 1 (lower case letters),
               1241 nucleotides of exon 1 (capital letters)
               and 285 nucleotides of 3' flanking region
               (lower case letters)

(x) SEQUENCE DESCRIPTION: SEQ ID NO:1:

agaat cgttacaaaa tatctatgac                                           25
cactaatggc tcttaaacca tactagtcac tgcattagat catattgctg aaaagtaaac     85
cattaagtca ccaagagagc tacttaacac acaaaaaatg tttagttata aatttgaacc    145
agtaacagaa ttgaaatacc agaaaatgtg gatctgattg tcttatttct tatttcccag    205

TAAACCTCAG TCAGAAACGC TGAAAGCAGG AGACTTGAGG ACACGAATTA GCCGATGTCA    265

AGTGTGCATG AAGAGGACAT AACATTTTGA AGAATTCCTT TTGTGTTTTA AAATGTGATA    325

TATATATATA TAAAATTCCT AGGATGCAGT GTCTCATTGT CCCCAACTTT ACTACTGCTG    385

CCGTCAATGG TGCTACTATA TATGATCAAG ATAACATGCT GACTAGTAAC CATGAAGATT    445
```

-continued

```
CAGATGTACC TCAGCAATGC GCCAGAGCAA AGTCTCTATT ATTTTTCTAC TAAAGAAATA    505

AGGAAGTGAA TTTACTTTTT GGGTCCAGAA TGACTTTCTC CAAGAATTAT AAGATGAAAA    565

TTATATATTT TGCCCAGTTA CTAAAATGGT ACATTAAAAA TTCAATTAAG AGAAGAGTCA    625

CATTGAGTAA AATAAAAGAC TGCAGTTTGT GGGAAGAATT ATTTTTCACG GTGCTACTAA    685

TCCTGCTGTA TCCCGGGTTT TTAATATAAA GGTGTTAAGC TTATTTTGCT TTGTAAGTAA    745

AGAATGTGTA TATTGTGAAC AGCCTTTTAG CTCAAAATGT TGAGTCATTT ACATATGACA    805

TAGCATGAAT CACTCTTTAC AGAAAATGTA GGAAACCCTA GAATACAGAC AGCAATATTT    865

TATATTCATG TTTATCAAAG TGAGAGGACT TATATTCCTA CATCAAGTTA CTACTGAGAG    925

TAAATTTATT TTGAGTTTTA TCCCGTAAGT TCTGTTTTGA TTTTTTTTAA AAAACAAACC    985

CTTTTAGTCA CTTTAATCAG AATTTTAAAT GTTCATGTTA CATACCAAAT TATAATATCT   1045

AATGGAGCAA TTTGTCTTTT GCTATATTCT CCAAGATTAT CTCTTAAGAC CATATGCCCC   1105

CTGTTTTAAT GTTTCTTACA TCTTGTTTTT ACTCATTTCT GACTGGACAA AGTTCTTCCA   1165

AACAATTCTG AGAAACAAAA ACACACACGC AGAATTAACA ATTCTTTTCC CTGTGCTTCT   1225

TATGTAAGAA TCCTCCTGTG GCCTCTGCTT GTACAGAACT GGGAAACAAC ACTTGGTTAG   1285

TCTCTTTTAA GTTACAAAAA GCCAATTGAT GTTTCTTATT CTTTTTAAAT TTTAAATATT   1345

TTGTTATAAA TACTCACAGG ATACCTTATT TCCCTAGCTA TCATCTCCTG ACTTAATGTT   1405

TTTTAAACCC ACCAATATAA ATTTAATTAA AGATATATGT Tgtaaggatg gtctgttgtg   1465
tatctcttca gcctgtgtgg aaaaaacccc tgctcattta cagatagatt accaatctgc   1525
acatcaacaa gtcatctctt cccagggaat cagtttctcc acgctttgat cactctgtta   1585
gtagatagaa aacatatagt aatgtaaact ttttccaatg aagaaaacta cctattggaa   1645
gacatttcca agataataaa tttcttgaca acattgtgtt aatggctaag aaaggaaaca   1705
actggcttct atttggggaa gaattc                                        1731
```

(2) INFORMATION FOR SEQ ID NO:2:

(i) SEQUENCE CHARACTERISTICS:
        (A) LENGTH:        503 base pairs
        (B) TYPE:          Nucleic acid
        (C) STRANDEDNESS:  Single
        (D) TOPOLOGY:      Linear (ii) MOLECULE TYPE:        Nucleotide-genomic DNA (iii) HYPOTHETICAL:        Irrelevant (iv) ANTI-SENSE:          Irrelevant (v) FRAGMENT TYPE:        Endonuclease restriction
        fragment (vi) ORIGINAL SOURCE:
        (A) ORGANISM:          Human
        (B) STRAIN:            Irrelevant
        (C) INDIVIDUAL ISOLATE:  Irrelevant
        (D) DEVELOPMENTAL STAGE: Irrelevant
        (E) HAPLOTYPE:         Irrelevant
        (F) TISSUE TYPE:       Liver
        (G) CELL TYPE:         Irrelevant
        (H) CELL LINE:         Irrelevant
        (I) ORGANELLE:         Irrelevant (vii) IMMEDIATE SOURCE:
        (A) LIBRARY:           Human genomic library in
            Charon 4A
        (B) CLONE:             ML-5

(viii) POSITION IN GENOME:

|  | (A) CHROMOSOME/SEGMENT: | X |
|---|---|---|
|  | (B) MAP POSITION: | q22 |
|  | (C) UNITS: | Irrelevant |

(ix) FEATURE:
    (A) NAME/KEY:              COL4A5 collagen gene
    (B) LOCATION:               Exon 2 region counted from
        3' end of gene
    (C) IDENTIFICATION METHOD:DNA sequencing
    (D) OTHER INFORMATION:    Sequence starts with 246
        nucleotides of intron 2 (lower case letters),
        followed by 173 nucleotides of exon 2 (capital
        letters) and ends with 84 nucleotides from
        downstream intron 1 (lower case letters).

(x) SEQUENCE DESCRIPTION: SEQ ID NO:2:

```
aagcttaaac ttcaaacagc ttctatccaa gcactgtgtt cccccctcaca catttttttgt    60
aacatatttt cataatctgc ctattacttt tttttgacta cccttggtgt ggatactatt   120
gtcttacctc tgggcctgtt ccttcactag atttgaattt ggccaagctc agcacacatc   180
tttggatatt cactaagcta ttatggcaca tgggtattgc ggcacatttt tccttgtctt   240
ttatagCATA CAAGTGCAGG GGCAGAAGGC TCAGGTCAAG CCCTAGCCTC CCCTGGTTCC   300
TGCTTGGAAG AGTTTCGTTC AGCTCCCTTC ATCGAATGTC ATGGGAGGGG TACCTGTAAC   360
TACTATGCCA ACTCCTACAG CTTTTGGCTG GCAACTGTAG ATGTGTCAGA CATGTTCAGg   420
taaagtgctt atagctttaa ttcaggtcca aagcttcctt cagagatgct agggaagaaa   480
gagacaattt atggatggtt tat                                          503
```

(2) INFORMATION FOR SEQ ID NO:3:

(i) SEQUENCE CHARACTERISTICS:
        (A) LENGTH:               360 base pairs
        (B) TYPE:                 Nucleic acid
        (C) STRANDEDNESS:       Single
        (D) TOPOLOGY:             Linear (ii) MOLECULE TYPE:         Nucleotide-genomic DNA (iii) HYPOTHETICAL:         Irrelevant (iv) ANTI-SENSE:            Irrelevant (v) FRAGMENT TYPE:          Endonuclease restriction
        fragment (vi) ORIGINAL SOURCE:
        (A) ORGANISM:             Human
        (B) STRAIN:               Irrelevant
        (C) INDIVIDUAL ISOLATE:  Irrelevant
        (D) DEVELOPMENTAL STAGE: Irrelevant
        (E) HAPLOTYPE:            Irrelevant
        (F) TISSUE TYPE:         Liver
        (G) CELL TYPE:           Irrelevant
        (H) CELL LINE:           Irrelevant
        (I) ORGANELLE:           Irrelevant (vii) IMMEDIATE SOURCE:
        (A) LIBRARY:              Human genomic in Charon
            4A vector
        (B) CLONE:                ML-5

(viii) POSITION IN GENOME:
        (A) CHROMOSOME/SEGMENT:   X
        (B) MAP POSITION:       q22
        (C) UNITS:                Irrelevant (ix) FEATURE:
        (A) NAME/KEY:              COL4A5 collagen gene
        (B) LOCATION:               Exon 3 region counted
            from 3' end of gene
        (C) IDENTIFICATION METHOD:DNA sequencing (D) OTHER INFORMATION: Sequence contains 141
nucleotides of intron 3 (lower case letters), 115
nucleotides of exon 3 (capital letters) and 104
nucleotides from downstream intron 2 (lower case
letters).

(x) SEQUENCE DESCRIPTION: SEQ ID NO:3:

```
aagtgcattt tttcacctttt tgtgatcatt gaaagagaca ttaatcggct tccatactaa    60
gaaggcttcc aatgaagcag gatggctact tctcacatgc tcactctgta gattatgttc   120
cttctccttt tcctttacca gATGTGCAGT ATGTGAAGCT CCAGCTGTGG TGATCGCAGT   180
TCACAGTCAG ACGATCCAGA TTCCCCATTG TCCTCAGGGA TGGGATTCTC TGTGGATTGG   240
TTATTCCTTC ATGATGgtat tttacactct tccttgcatt tgtcatcata gctgactgtc   300
cattccatct acatttcttc ccaatatgag gaatccctgt catttgcata ataagaagct   360
```

(2) INFORMATION FOR SEQ ID NO:4:

(i) SEQUENCE CHARACTERISTICS:
        (A) LENGTH:           433 base pairs
        (B) TYPE:             Nucleic acid
        (C) STRANDEDNESS:     Single
        (D) TOPOLOGY:         Linear (ii) MOLECULE TYPE:           Nucleotide-genomic DNA (iii) HYPOTHETICAL:            Irrelevant (iv) ANTI-SENSE:              Irrelevant (v) FRAGMENT TYPE:           Endonuclease restriction
        fragment (vi) ORIGINAL SOURCE:
        (A) ORGANISM:          Human
        (B) STRAIN:            Irrelevant
        (C) INDIVIDUAL ISOLATE: Irrelevant
        (D) DEVELOPMENTAL STAGE: Irrelevant
        (E) HAPLOTYPE:         Irrelevant
        (F) TISSUE TYPE:       Liver
        (G) CELL TYPE:         Irrelevant
        (H) CELL LINE:         Irrelevant
        (I) ORGANELLE:         Irrelevant (vii) IMMEDIATE SOURCE:
        (A) LIBRARY:           Human genomic in Charon 4
           A vector
        (B) CLONE:             ML-5

(viii) POSITION IN GENOME:
        (A) CHROMOSOME/SEGMENT:       X
        (B) MAP POSITION:             q22
        (C) UNITS:                    Irrelevant (ix) FEATURE:
        (A) NAME/KEY:              COL4A5 collagen gene
        (B) LOCATION:           Exon 4 region counted
           from 3' end of gene
        (C) IDENTIFICATION METHOD:DNA sequencing
        (D) OTHER INFORMATION:   Sequence contains 138
           nucleotides of intron 4 (lower case letters), 178
           nucleotides of exon 4 (capital letters) and 117
           nucleotides from downstream intron 3 (lower case
           letters).

(x) SEQUENCE DESCRIPTION: SEQ ID NO:4:

```
aactaaggaa atatagtata tttattacct atgaaaggct ggcaagtttc cttgaaaggc    60
tgtttgctat tgttttagaa gaaaccaaag tatcattatc acgcagtcct ttactgtttt   120
ctctccaaat cttctagGG ACGGCTGGCA GCTGCCTTCG TCGCTTTAGT ACCATGCCTT   180
TCATGTTCTG CAACATCAAT AATGTTTGCA ACTTTGCTTC AAGAAATGAC TATTCTTACT   240
```

-continued

```
GGCTCTCTAC CCCAGAGCCC ATGCCAATGA GCATGCAACC CCTAAAGGGC CAGAGCATCC      300

AGCCATTCAT TAGTCGgtaa ggcattgatt tagctgtgac ttttaccaat ccccagttag      360
ttagctagtc agatttgagt ccaaagctaa caatctgatg atattcctcc taggttaggt      420
agaacagagg tac                                                         433
```

(2) INFORMATION FOR SEQ ID NO:5:

(i) SEQUENCE CHARACTERISTICS:
        (A) LENGTH:         461 base pairs
        (B) TYPE:           Nucleic acid
        (C) STRANDEDNESS:   Single
        (D) TOPOLOGY:       Linear (ii) MOLECULE TYPE:       Nucleotide-genomic DNA (iii) HYPOTHETICAL:       Irrelevant (iv) ANTI-SENSE:         Irrelevant (v) FRAGMENT TYPE:       Endonuclease restriction
        fragment (vi) ORIGINAL SOURCE:
        (A) ORGANISM:       Human
        (B) STRAIN:         Irrelevant
        (C) INDIVIDUAL ISOLATE: Irrelevant
        (D) DEVELOPMENTAL STAGE: Irrelevant
        (E) HAPLOTYPE:      Irrelevant
        (F) TISSUE TYPE:    Lung
        (G) CELL TYPE:      Irrelevant
        (H) CELL LINE:      Irrelevant
        (I) ORGANELLE:      Irrelevant (vii) IMMEDIATE SOURCE:
        (A) LIBRARY:       Human genomic in lambda
            FIX and EMBL vectors
        (B) CLONE:         FM-13 and EB-4

(viii) POSITION IN GENOME:
        (A) CHROMOSOME/SEGMENT:   X
        (B) MAP POSITION:   q22
        (C) UNITS:         Irrelevant (ix) FEATURE:
        (A) NAME/KEY:       COL4A5 collagen gene
        (B) LOCATION:      Exon 5 region counted
            from 3' end of gene
        (C) IDENTIFICATION METHOD:DNA sequencing
        (D) OTHER INFORMATION:  Sequence contains 159
            nucleotides of intron 5 (lower case letters), 213
            nucleotides of exon 5 (capital letters) and 89
            nucleotides from downstream intron 4 (lower case
            letters).

(x) SEQUENCE DESCRIPTION: SEQ ID NO:5:

```
tttgtctcct agcccatgat atctgacaat gcctttatag acactctata aatatcaaat       60
aaattaacta gtcaaatgag gtcataatgt tttgtcaata tccataagag tggatcagag      120
cttacttaat cttgtatact gattatttcg tggaaatagG TACCCGTGGT TTGGATGGTC      180

CCCCTGGTCC AGATGGATTG CAAGGTCCCC CAGGTCCCCC TGGAACCTCC TCTGTTGCAC      240

ATGGATTTCT TATTACACGC CACAGCCAGA CAACGGATGC ACCACAATGC CCACAGGGAA      300

CACTTCAGGT CTATGAAGGC TTTTCTCTCC TGTATGTACA AGGAAATAAA AGAGCCCACG      360

GTCAAGACTT GGgtgagata atcaatatct aatttcctac tgtgcctttt gtttttgttt      420
cagaaatcct gttgggttct agagtagcct tggccaaagt g                          461
```

(2) INFORMATION FOR SEQ ID NO:6:

```
        (i) SEQUENCE CHARACTERISTICS:
            (A) LENGTH:           308 base pairs
            (B) TYPE:             Nucleic acid
            (C) STRANDEDNESS:     Single
            (D) TOPOLOGY:         Linear (ii) MOLECULE TYPE:             Nucleotide-genomic DNA (iii) HYPOTHETICAL:               Irrelevant (iv) ANTI-SENSE:                 Irrelevant (v) FRAGMENT TYPE:              Endonuclease restriction
            fragment (vi) ORIGINAL SOURCE:
            (A) ORGANISM:           Human
            (B) STRAIN:             Irrelevant
            (C) INDIVIDUAL ISOLATE: Irrelevant
            (D) DEVELOPMENTAL STAGE: Irrelevant
            (E) HAPLOTYPE:          Irrelevant
            (F) TISSUE TYPE:        Lung
            (G) CELL TYPE:          Irrelevant
            (H) CELL LINE:          Irrelevant
            (I) ORGANELLE:          Irrelevant (vii) IMMEDIATE SOURCE:
            (A) LIBRARY:            Human genomic in lambda
                Fix vector
            (B) CLONE:              FM-13

(viii) POSITION IN GENOME:
            (A) CHROMOSOME/SEGMENT:        X
            (B) MAP POSITION:       q22
            (C) UNITS:              Irrelevant (ix) FEATURE:
            (A) NAME/KEY:               COL4A5 collagen gene
            (B) LOCATION:           Exon 6 region counted
                from 3' end of gene
            (C) IDENTIFICATION METHOD:DNA sequencing
            (D) OTHER INFORMATION:  Sequence contains 78
                nucleotides from intron 6 (lower case letters),
                99 nucleotides of exon 6 (capital letters) and
                131 nucleotides from downstream intron 5 (lower
                case letters).

(x) SEQUENCE DESCRIPTION: SEQ ID NO:6:

agaaccttat gtctcctaga tctgtccaga tgtgaaaata ttctactcat atttgaatgc        60
ctcattcttt tcctgtagGT CCAACTGGCC CTCCAGGAGA TCCTGGACGC AATGGACTCC       120

CTGGCTTTGA TGGTGCAGGA GGGCGCAAAG GAGACCCAGG TCTGCCAGGA CAGCCAGgta       180
agacaagtaa aacatgctgt tggtggaggg aaagtctttg agtctgagag acctctggac       240
atagggcctc cacttagagc tgtgagatct tctcttgatg ttagcatagc tgactggtga       300
atgtggac                                                               308

(2) INFORMATION FOR SEQ ID NO:7:

(i) SEQUENCE CHARACTERISTICS:
            (A) LENGTH:           280 base pairs
            (B) TYPE:             Nucleic acid
            (C) STRANDEDNESS:     Single
            (D) TOPOLOGY:         Linear (ii) MOLECULE TYPE:             Nucleotide-genomic DNA (iii) HYPOTHETICAL:               Irrelevant (iv) ANTI-SENSE:                 Irrelevant (v) FRAGMENT TYPE:              Endonuclease restriction
            fragment
```

```
        (vi) ORIGINAL SOURCE:
             (A) ORGANISM:               Human
             (B) STRAIN:                 Irrelevant
             (C) INDIVIDUAL ISOLATE:     Irrelevant
             (D) DEVELOPMENTAL STAGE:    Irrelevant
             (E) HAPLOTYPE:              Irrelevant
             (F) TISSUE TYPE:            Lung
             (G) CELL TYPE:              Irrelevant
             (H) CELL LINE:              Irrelevant
             (I) ORGANELLE:              Irrelevant (vii) IMMEDIATE SOURCE:
             (A) LIBRARY:                Human genomic in lambda
                   Fix vector
             (B) CLONE:                  FM-13 and F-2

(viii) POSITION IN GENOME:
             (A) CHROMOSOME/SEGMENT:            X
             (B) MAP POSITION:           q22
             (C) UNITS:                  Irrelevant (ix) FEATURE:
             (A) NAME/KEY:                    COL4A5 collagen gene
             (B) LOCATION:               Exon 7 region counted
                   from 3' end of gene
             (C) IDENTIFICATION METHOD:DNA sequencing
             (D) OTHER INFORMATION:      Sequence contains 62
                   nucleotides from intron 7 (lower case letters),
                   129 nucleotides of exon 7 (capital letters) and
                   89 nucleotides from downstream intron 6 (lower
                   case letters).

(x) SEQUENCE DESCRIPTION: SEQ ID NO:7:

tttggcttcc atttcttgta acctttctct ttcccttcaa atttgtgtgt tttgtctcat     60
agGTCCTCCT GGATTACCTG GTCCTTCAGG ACAGAGTATC ATAATTAAAG GAGATGCTGG    120

TCCTCCAGGA ATCCCTGGCC AGCCTGGGCT AAAGGGTCTA CCAGGACCCC AAGGACCTCA    180

AGGCTTACCA Ggtaccaatg cagatcatct ttattatcat tattatactt ttaatttctg    240
ggatacatgt gcagaatgta caggtttgtt acataggtat                          280

(2) INFORMATION FOR SEQ ID NO:8:

(i) SEQUENCE CHARACTERISTICS:
             (A) LENGTH:                 206 base pairs
             (B) TYPE:                   Nucleic acid
             (C) STRANDEDNESS:           Single
             (D) TOPOLOGY:               Linear (ii) MOLECULE TYPE:              Nucleotide-genomic DNA (iii) HYPOTHETICAL:               Irrelevant (iv) ANTI-SENSE:                 Irrelevant (v) FRAGMENT TYPE:              Endonuclease restriction
                 fragment (vi) ORIGINAL SOURCE:
             (A) ORGANISM:               Human
             (B) STRAIN:                 Irrelevant
             (C) INDIVIDUAL ISOLATE:     Irrelevant
             (D) DEVELOPMENTAL STAGE:    Irrelevant
             (E) HAPLOTYPE:              Irrelevant
             (F) TISSUE TYPE:            Lung
             (G) CELL TYPE:              Irrelevant
             (H) CELL LINE:              Irrelevant
             (I) ORGANELLE:              Irrelevant (vii) IMMEDIATE SOURCE:
             (A) LIBRARY:                Human genomic in lambda
                   Fix vector
             (B) CLONE:                  FM-13 and F-2
```

(viii) POSITION IN GENOME:
        (A) CHROMOSOME/SEGMENT:        X
        (B) MAP POSITION:              q22
        (C) UNITS:                     Irrelevant (ix) FEATURE:
        (A) NAME/KEY:                  COL4A5 collagen gene
        (B) LOCATION:                  Exon region 8 counted
            from 3' end of gene
        (C) IDENTIFICATION METHOD:DNA sequencing
        (D) OTHER INFORMATION:    Sequence contains 33
            nucleotides of intron 8 (lower case letters), the
            72 nucleotides exon 8 (capital letters) and 101
            nucleotides of intron 7 (lower case letters).

(x) SEQUENCE DESCRIPTION: SEQ ID NO:8:

tttgc cataaaactg tatgtacctt ctgtgcagGC ATGAAAGGAC CCAGTGGAGT      55

ACCTGGATCA GCTGGCCCTG AGGGGGAACC GGGACTTATT GGTCCTCCAG gtaagactta    115
ttcctgaaga tagttatacc tgatacttag atgctttaaa gaatttgaaa gttttcattc    175
tgtctttcag ccagaccatc ggaggctaag t                                   206

(2) INFORMATION FOR SEQ ID NO:9:

(i) SEQUENCE CHARACTERISTICS:
        (A) LENGTH:                    365 base pairs
        (B) TYPE:                      Nucleic acid
        (C) STRANDEDNESS:              Single
        (D) TOPOLOGY:                  Linear (ii) MOLECULE TYPE:                 Nucleotide-genomic DNA (iii) HYPOTHETICAL:                  Irrelevant (iv) ANTI-SENSE:                    Irrelevant (v) FRAGMENT TYPE:                 Endonuclease restriction
        fragment (vi) ORIGINAL SOURCE:
        (A) ORGANISM:                  Human
        (B) STRAIN:                    Irrelevant
        (C) INDIVIDUAL ISOLATE:        Irrelevant
        (D) DEVELOPMENTAL STAGE:       Irrelevant
        (E) HAPLOTYPE:                 Irrelevant
        (F) TISSUE TYPE:               Lung
        (G) CELL TYPE:                 Irrelevant
        (H) CELL LINE:                 Irrelevant
        (I) ORGANELLE:                 Irrelevant (vii) IMMEDIATE SOURCE:
        (A) LIBRARY:                   Human genomic in lambda
            Fix vector
        (B) CLONE:                     FM-13 and F-2

(viii) POSITION IN GENOME:
        (A) CHROMOSOME/SEGMENT:        X
        (B) MAP POSITION:              q22
        (C) UNITS:                     Irrelevant (ix) FEATURE:
        (A) NAME/KEY:                  COL4A5 collagen gene
        (B) LOCATION:                  Exon region 9 counted
            from 3' end of gene
        (C) IDENTIFICATION METHOD:DNA sequencing
        (D) OTHER INFORMATION:    Sequence contains 192
            nucleotides of intron 9 (lower case letters),
            followed by 73 nucleotides exon 9 (capital
            letters), and 100 nucleotides intron 8 (lower
            case letters).

(x) SEQUENCE DESCRIPTION: SEQ ID NO:9:

aaactatgaa tcaaggaggt taaataatca actcaattca cacaagataa tataaggcaa      60

```
aattgagatt acagtcttgg aagtttgact ctagaaatag tgctatatgc cactatgtaa      120
ttcttatgcc ctcaatcacc ttcctcccct cgctgcaatt tttttgtaac attaatgatt      180
ttatttattc agGGTAATCC TGGCCGGCCG GGTCTCAATG GAATGAAAGG AGATCCTGGT      240

CTCCCTGGTG TTCCAGGATT CCCAGgtatt tgaagggatt tttgtggttt ccctttatat      300
taaactcctc tgggacaaga tagccatttt ctgatttgac tgggtaaagg ttgtagccct      360
gttgc                                                                  365
```

(2) INFORMATION FOR SEQ ID NO:10:

(i) SEQUENCE CHARACTERISTICS:
        (A) LENGTH:         286 base pairs
        (B) TYPE:           Nucleic acid
        (C) STRANDEDNESS:   Single
        (D) TOPOLOGY:       Linear (ii) MOLECULE TYPE:      Nucleotide-genomic DNA (iii) HYPOTHETICAL:       Irrelevant (iv) ANTI-SENSE:         Irrelevant (v) FRAGMENT TYPE:      Endonuclease restriction
        fragment (vi) ORIGINAL SOURCE:
        (A) ORGANISM:      Human
        (B) STRAIN:        Irrelevant
        (C) INDIVIDUAL ISOLATE: Irrelevant
        (D) DEVELOPMENTAL STAGE: Irrelevant
        (E) HAPLOTYPE:     Irrelevant
        (F) TISSUE TYPE:   Lung
        (G) CELL TYPE:     Irrelevant
        (H) CELL LINE:     Irrelevant
        (I) ORGANELLE:     Irrelevant (vii) IMMEDIATE SOURCE:
        (A) LIBRARY:       Human genomic in lambda
            Fix vector
        (B) CLONE:         F-7

(viii) POSITION IN GENOME:
        (A) CHROMOSOME/SEGMENT:   X
        (B) MAP POSITION:   q22
        (C) UNITS:         Irrelevant (ix) FEATURE:
        (A) NAME/KEY:         COL4A5 collagen gene
        (B) LOCATION:      Exon 10 region from 3'
            end of gene
        (C) IDENTIFICATION METHOD:DNA sequencing
        (D) OTHER INFORMATION:   Sequence contains 86
            nucleotides of intron 10 (lower case letters),
            134 nucleotides exon 10 (capital letters) and 66
            nucleotides of downstream intron 9 (lower case
            letters).

(x) SEQUENCE DESCRIPTION: SEQ ID NO:10:

```
gaagatgact gatattttaa aagcctgact tttatgctac tcttaacact atactgaaat       60
gtcgtcattt gctgtggatt attaagGTCT ACCAGGTCCA GAAGGTCCTC CAGGTCTCCC      120

TGGAAATGGA GGTATTAAAG GAGAGAAGGG AAATCCAGGC CAACCTGGGC TACCTGGCTT      180

GCCTGGTTTG AAAGGAGATC AAGGACCACC AGGACTCCAG gtaggaaatg gaagtagata      240
tctgatgaga gaagaatgtg ggtgtttgta ttcaaaatgt gaattc                     286
```

(2) INFORMATION FOR SEQ ID NO:11:

(i) SEQUENCE CHARACTERISTICS:
        (A) LENGTH:         507 base pairs

```
            (B) TYPE:                   Nucleic acid
            (C) STRANDEDNESS:           Single
            (D) TOPOLOGY:               Linear (ii) MOLECULE TYPE:               Nucleotide-genomic DNA (iii) HYPOTHETICAL:                Irrelevant (iv) ANTI-SENSE:                  Irrelevant (v) FRAGMENT TYPE:               Endonuclease restriction
              fragment (vi) ORIGINAL SOURCE:
            (A) ORGANISM:               Human
            (B) STRAIN:                 Irrelevant
            (C) INDIVIDUAL ISOLATE:     Irrelevant
            (D) DEVELOPMENTAL STAGE:    Irrelevant
            (E) HAPLOTYPE:              Irrelevant
            (F) TISSUE TYPE:            Lung
            (G) CELL TYPE:              Irrelevant
            (H) CELL LINE:              Irrelevant
            (I) ORGANELLE:              Irrelevant (vii) IMMEDIATE SOURCE:
            (A) LIBRARY:                Human genomic in lambda
                  Fix vector
            (B) CLONE:                  F-7

(viii) POSITION IN GENOME:
            (A) CHROMOSOME/SEGMENT:          X
            (B) MAP POSITION:           q22
            (C) UNITS:                  Irrelevant (ix) FEATURE:
            (A) NAME/KEY:                    COL4A5 collagen gene
            (B) LOCATION:               Exon 11 region from 3'
                  end of gene
            (C) IDENTIFICATION METHOD:DNA sequencing
            (D) OTHER INFORMATION:      Sequence contains 94
                  nucleotides of intron 11 (lower case letters),
                  186 nucleotides of exon 11 (capital letters) and
                  227 nucleotides of downstream intron 10 (lower
                  case letters).

(x) SEQUENCE DESCRIPTION: SEQ ID NO:11:

ccattaattg ccctaatgta tgtgaatagc taaccttata agcaagcttg taactcggta      60
ttatttatct tctaattata ctttactttc atagGCCAAA AGGGTGATGG AGGATTACCT     120

GGGATTCCAG GAAATCCTGG CCTTCCAGGT CCAAAGGGCG AACCAGGCTT TCACGGTTTC     180

CCTGGTGTGC AGGGTCCCCC AGGCCCTCCT GGTTCTCCGG GTCCAGCTCT GGAAGGACCT     240

AAAGGCAACC CTGGGCCCCA AGGTCCTCCT GGGAGACCAG gtatgtccgt gagtggtagg     300
agaatggtct atttattagt ccatgtattt cgttttgctg gcaggttatt cagtctttaa     360
gactttagaa ttttccggt gcattggagg atgttaaaaa aaagacttta aaatttgtga      420
tataacttct tacaagtaaa tagcttggtt catagctaac tccatctatt tccatggttc     480
taataatttg ctttagtaat gcatttt                                          507

(2) INFORMATION FOR SEQ ID NO:12:

(i) SEQUENCE CHARACTERISTICS:
            (A) LENGTH:                 191 base pairs
            (B) TYPE:                   Nucleic acid
            (C) STRANDEDNESS:           Single
            (D) TOPOLOGY:               Linear (ii) MOLECULE TYPE:                Nucleotide-genomic DNA (iii) HYPOTHETICAL:                 Irrelevant (iv) ANTI-SENSE:                   Irrelevant
```

```
        (v) FRAGMENT TYPE:              Endonuclease restriction
                fragment (vi) ORIGINAL SOURCE:
            (A) ORGANISM:               Human
            (B) STRAIN:                 Irrelevant
            (C) INDIVIDUAL ISOLATE:     Irrelevant
            (D) DEVELOPMENTAL STAGE:    Irrelevant
            (E) HAPLOTYPE:              Irrelevant
            (F) TISSUE TYPE:            Lung
            (G) CELL TYPE:              Irrelevant
            (H) CELL LINE:              Irrelevant
            (I) ORGANELLE:              Irrelevant (vii) IMMEDIATE SOURCE:
            (A) LIBRARY:                genomic in lambda Fix
                vector
            (B) CLONE:                  F-7

(viii) POSITION IN GENOME:
            (A) CHROMOSOME/SEGMENT:           X
            (B) MAP POSITION:           q22
            (C) UNITS:                  Irrelevant (ix) FEATURE:
            (A) NAME/KEY:                     COL4A5 collagen gene
            (B) LOCATION:               Exon 12 region from 3'
                end of gene
            (C) IDENTIFICATION METHOD:DNA sequencing
            (D) OTHER INFORMATION:      Sequence contains 53
                nucleotides from intron 12 (lower case letters),
                51 nucleotides exon 12 (capital letters) and 87
                nucleotides of downstream intron 11 (lower case
                letters).

(x) SEQUENCE DESCRIPTION: SEQ ID NO:12:

cagttgtatt atccacttga gtttttgttt tgttttgttt tgtactctga cagGTCAACC      60

AGGCTTTGGA AACCCAGGAC CCCCTGGACT TCCAGGACTT TCTGgtaaac cttaataaaa    120
catgctaaat caatctataa taaaatgaga ttatttccaa atacatctat ttttccatct    180 ccaccttta c                                                          191

(2) INFORMATION FOR SEQ ID NO:13:

(i) SEQUENCE CHARACTERISTICS:
            (A) LENGTH:                 349 base pairs
            (B) TYPE:                   Nucleic acid
            (C) STRANDEDNESS:           Single
            (D) TOPOLOGY:               Linear (ii) MOLECULE TYPE:              Nucleotide-genomic DNA (iii) HYPOTHETICAL:               Irrelevant (iv) ANTI-SENSE:                 Irrelevant (v) FRAGMENT TYPE:              Endonuclease restriction
                fragment (vi) ORIGINAL SOURCE:
            (A) ORGANISM:               Human
            (B) STRAIN:                 Irrelevant
            (C) INDIVIDUAL ISOLATE:     Irrelevant
            (D) DEVELOPMENTAL STAGE:    Irrelevant
            (E) HAPLOTYPE:              Irrelevant
            (F) TISSUE TYPE:            Lung
            (G) CELL TYPE:              Irrelevant
            (H) CELL LINE:              Irrelevant
            (I) ORGANELLE:              Irrelevant (vii) IMMEDIATE SOURCE:
            (A) LIBRARY:                genomic library in lambda
                Fix vector
            (B) CLONE:                  F-7
```

```
    (viii) POSITION IN GENOME:
           (A) CHROMOSOME/SEGMENT:          X
           (B) MAP POSITION:         q22
           (C) UNITS:                Irrelevant (ix) FEATURE:
           (A) NAME/KEY:                    COL4A5 collagen gene
           (B) LOCATION:             Exon 13 region from 3'
               end of gene
           (C) IDENTIFICATION METHOD:DNA sequencing
           (D) OTHER INFORMATION:    Sequence contains 181
               nucleotides from intron 13 (lower case letters),
               99 nucleotides exon 13 (capital letters) and 69
               nucleotides of downstream intron 12 (lower case
               letters).

(x) SEQUENCE DESCRIPTION: SEQ ID NO:13:

agatgctgaa tgactattcc ttattttcat tatcctcctt catattttta taacatttg      60 tgatccaaag gagtgtctca aaagcacctt gtttcttttg gataaagaag ggagcatatg    120
gaagtaaaag ggagttggaa attggaaaac tgggtgtaac ctgctgtact caattttta    180 gGTGGTGGAG GTCATCCTGG GCAACCAGGG CCTCCAGGCG AAAAAGGCAA ACCCGGTCAA    240

GATGGTATTC CTGGACCAGC TGGACAGAAG GGTGAACCAG gtgctgtagt ttttcatttt    300 tcctatttt ctaattttct ctgtgttgaa tttaacttgc cttttatt                  349

(2) INFORMATION FOR SEQ ID NO:14:

(i) SEQUENCE CHARACTERISTICS:
           (A) LENGTH:               292 base pairs
           (B) TYPE:                 Nucleic acid
           (C) STRANDEDNESS:         Single
           (D) TOPOLOGY:             Linear (ii) MOLECULE TYPE:              Nucleotide-genomic DNA (iii) HYPOTHETICAL:               Irrelevant (iv) ANTI-SENSE:                 Irrelevant (v) FRAGMENT TYPE:              Irrelevant (vi) ORIGINAL SOURCE:
           (A) ORGANISM:             Human
           (B) STRAIN:               Irrelevant
           (C) INDIVIDUAL ISOLATE:   Irrelevant
           (D) DEVELOPMENTAL STAGE:  Irrelevant
           (E) HAPLOTYPE:            Irrelevant
           (F) TISSUE TYPE:          Lung
           (G) CELL TYPE:            Irrelevant
           (H) CELL LINE:            Irrelevant
           (I) ORGANELLE:            Irrelevant (vii) IMMEDIATE SOURCE:
           (A) LIBRARY:              Human genomic in lambda
                Fix vector
           (B) CLONE:                F-7

(viii) POSITION IN GENOME:
           (A) CHROMOSOME/SEGMENT:          X
           (B) MAP POSITION:         q22
           (C) UNITS:                Irrelevant (ix) FEATURE:
           (A) NAME/KEY:                    COL4A5 collagen gene
           (B) LOCATION:             Exon 13 region from 3'
               end of gene
           (C) IDENTIFICATION METHOD:DNA sequencing
           (D) OTHER INFORMATION:    Sequence contains 113
               nucleotides from intron 14 (lower case letters),
               81 nucleotides exon 14 (capital letters) and 98
               nucleotides of downstream sequence (intron 13,
               lower case letters).
```

(x) SEQUENCE DESCRIPTION: SEQ ID NO:14:

```
ttcttttgt tcttcactgt ttctatgcta gcactataaa ttgtaagttt gaattgtagc        60
tcttaaagca atgcagtttt tctttcattt ttaaattgag ctctttactc tagGAACCCC      120

AGGCCCTCCT GGACCAAAAG GTATTAGTGG CCCTCCTGGG AACCCCGGCC TTCCAGGAGA      180

ACCTGGTCCT GTAGgtaagc atgaaaaata acagtttgct gttttataaa actaatgttt     240
atcatattaa gtttgggaaa gtcaaatcat gttcagctgt gaacattttc aa             292
```

(2) INFORMATION FOR SEQ ID NO:15:

(i) SEQUENCE CHARACTERISTICS:
        (A) LENGTH:         127 base pairs
        (B) TYPE:           Nucleic acid
        (C) STRANDEDNESS:   Single
        (D) TOPOLOGY:      Linear (ii) MOLECULE TYPE:       Nucleotide-genomic DNA (iii) HYPOTHETICAL:       Irrelevant (iv) ANTI-SENSE:         Irrelevant (v) FRAGMENT TYPE:       PCR amplified fragment (vi) ORIGINAL SOURCE:
        (A) ORGANISM:      Human
        (B) STRAIN:        Irrelevant
        (C) INDIVIDUAL ISOLATE:  Irrelevant
        (D) DEVELOPMENTAL STAGE: Irrelevant
        (E) HAPLOTYPE:     Irrelevant
        (F) TISSUE TYPE:   Leukocyte
        (G) CELL TYPE:     Irrelevant
        (H) CELL LINE:     Irrelevant
        (I) ORGANELLE:     Irrelevant (vii) IMMEDIATE SOURCE:
        (A) LIBRARY:       None
        (B) CLONE:         PCR amplified exon 15
            cloned in M13 vector (viii) POSITION IN GENOME:
        (A) CHROMOSOME/SEGMENT:    X
        (B) MAP POSITION:    q22
        (C) UNITS:          Irrelevant (ix) FEATURE:
        (A) NAME/KEY:       COL4A5 collagen gene
        (B) LOCATION:        Exon 15 counted from 3'
            end of gene
        (C) IDENTIFICATION METHOD:DNA sequencing
        (D) OTHER INFORMATION:   The sequence contains the
            127 nucleotides exon 15.

(x) SEQUENCE DESCRIPTION: SEQ ID NO:15:

```
GGTGAGCCTG GTCTGCCTGG ATACCCAGGG AACCCTGGTA TCAAAGGTTC TGTGGGAGAT       60

CCTGGTTTGC CCGGATTACC AGGAACCCCT GGAGCAAAAG GACAACCAGG CCTTCCTGGA      120

TTCCCAG                                                                 127
```

(2) INFORMATION FOR SEQ ID NO:16:

(i) SEQUENCE CHARACTERISTICS:
        (A) LENGTH:         264 base pairs
        (B) TYPE:           Nucleic acid
        (C) STRANDEDNESS:   Single
        (D) TOPOLOGY:      Linear (ii) MOLECULE TYPE:       Nucleotide-genomic DNA (iii) HYPOTHETICAL:       Irrelevant

```
        (iv) ANTI-SENSE:                    Irrelevant (v) FRAGMENT TYPE:                 Endonuclease restriction
                 fragment (vi) ORIGINAL SOURCE:
             (A) ORGANISM:                  Human
             (B) STRAIN:                    Irrelevant
             (C) INDIVIDUAL ISOLATE:        Irrelevant
             (D) DEVELOPMENTAL STAGE:       Irrelevant
             (E) HAPLOTYPE:                 Irrelevant
             (F) TISSUE TYPE:               Lung
             (G) CELL TYPE:                 Irrelevant
             (H) CELL LINE:                 Irrelevant
             (I) ORGANELLE:                 Irrelevant (vii) IMMEDIATE SOURCE:
             (A) LIBRARY:                   Human genomic in lambda
                 FIX vector
             (B) CLONE:                     F8

(viii) POSITION IN GENOME:
             (A) CHROMOSOME/SEGMENT:            X
             (B) MAP POSITION:              q22
             (C) UNITS:                     Irrelevant (ix) FEATURE:
             (A) NAME/KEY:                     COL4A5 collagen gene
             (B) LOCATION:                  Exon 16 region from 3'
                 end of gene
             (C) IDENTIFICATION METHOD:DNA sequencing
             (D) OTHER INFORMATION:    The sequence contains 100
                 nucleotides from intron 16 (lower case letters),
                 140 nucleotides exon 16 (capital letters) and 24
                 nucleotides of intron 15 (lower case letters).

(x) SEQUENCE DESCRIPTION: SEQ ID NO:16:

ggagcttttt aaaaatcttt ttgctttgtc atatgcatct tagataatcc acaagtaaag        60
catattttgt aaaatattat atatcacata ttttcaacag GGCCTCAGGG TGTGGAAGGG       120

CCTCCTGGAC CTTCTGGAGT TCCTGGACAA CCTGGCTCCC CAGGATTACC TGGACAGAAA       180

GGCGACAAAG GTGATCCTGG TATTTCAAGC ATTGGTCTTC CAGGTCTTCC TGGTCCAAAG       240
gtaatctttg gcatatagtt ttag                                              264

(2) INFORMATION FOR SEQ ID NO:17:

(i) SEQUENCE CHARACTERISTICS:
             (A) LENGTH:                    330 base pairs
             (B) TYPE:                      Nucleic acid
             (C) STRANDEDNESS:              Single
             (D) TOPOLOGY:                  Linear (ii) MOLECULE TYPE:                 Nucleotide-genomic DNA (iii) HYPOTHETICAL:                  Irrelevant (iv) ANTI-SENSE:                    Irrelevant (v) FRAGMENT TYPE:                 Irrelevant (vi) ORIGINAL SOURCE:
             (A) ORGANISM:                  Human
             (B) STRAIN:                    Irrelevant
             (C) INDIVIDUAL ISOLATE:        Irrelevant
             (D) DEVELOPMENTAL STAGE:       Irrelevant
             (E) HAPLOTYPE:                 Irrelevant
             (F) TISSUE TYPE:               Lung
             (G) CELL TYPE:                 Irrelevant
             (H) CELL LINE:                 Irrelevant
             (I) ORGANELLE:                 Irrelevant (vii) IMMEDIATE SOURCE:
             (A) LIBRARY:                   Human genomic in lambda
```

```
                    FIX vector
          (B) CLONE:                    F8

(viii) POSITION IN GENOME:
          (A) CHROMOSOME/SEGMENT:       X
          (B) MAP POSITION:             q22
          (C) UNITS:                    Irrelevant (ix) FEATURE:
          (A) NAME/KEY:                 COL4A5 collagen gene
          (B) LOCATION:                 Exon 17 region from 3'
              end of gene
          (C) IDENTIFICATION METHOD:DNA sequencing
          (D) OTHER INFORMATION:   The sequence contains 84
              nucleotides of intron 18 (lower case letters), 90
              nucleotides of exon 17 (capital letters) and 156
              nucleotides of intron 17 (lower case letters).

(x) SEQUENCE DESCRIPTION: SEQ ID NO:17:

attttaatga ctatccattc ccatgaaacc agacaacccc aatattgcta cattgtctta      60
attttaccaa tttgaccttt ctagGTCCCA AAGGTAACCC TGGTCTCCCT GGACAGCCAG     120

GTCTTATAGG ACCTCCTGGA CTTAAAGGAA CCATCGGTGA TATGGGTTTT CCAGgtgagt    180
gatgaaaatc ttccaaatat ttagtcccat taatgaaagg tggttcaata tctctttttt    240
tgtcagaaaa gaggctggtg ttgatagaat cagactgaaa cgatatctga ggtaatcagt    300
gggtagtgtt ctcttgttac acaaatattt                                     330

(2) INFORMATION FOR SEQ ID NO:18:

(i) SEQUENCE CHARACTERISTICS:
          (A) LENGTH:                   307 base pairs
          (B) TYPE:                     Nucleic acid
          (C) STRANDEDNESS:             Single
          (D) TOPOLOGY:                 Linear (ii) MOLECULE TYPE:                Nucleotide-genomic DNA (iii) HYPOTHETICAL:                 Irrelevant (iv) ANTI-SENSE:                   Irrelevant (v) FRAGMENT TYPE:                Endonuclease restriction
              fragment (vi) ORIGINAL SOURCE:
          (A) ORGANISM:                 Human
          (B) STRAIN:                   Irrelevant
          (C) INDIVIDUAL ISOLATE:       Irrelevant
          (D) DEVELOPMENTAL STAGE:      Irrelevant
          (E) HAPLOTYPE:                Irrelevant
          (F) TISSUE TYPE:              Lung
          (G) CELL TYPE:                Irrelevant
          (H) CELL LINE:                Irrelevant
          (I) ORGANELLE:                Irrelevant (vii) IMMEDIATE SOURCE:
          (A) LIBRARY:                  Human genomic in lambda
              FIX vector
          (B) CLONE:                    F8

(viii) POSITION IN GENOME:
          (A) CHROMOSOME/SEGMENT:       X
          (B) MAP POSITION:             q22
          (C) UNITS:                    Irrelevant (ix) FEATURE:
          (A) NAME/KEY:                 COL4A5 collagen gene
          (B) LOCATION:                 Exon 18 region from 3'
              end of gene
          (C) IDENTIFICATION METHOD:DNA sequencing
          (D) OTHER INFORMATION:   The sequence contains 159
              nucleotides from intron 18 (lower case letters),
              99 nucleotides of exon 18 (capital letters) and
```

49 nucleotides of intron 17 (lower case letters).

(x) SEQUENCE DESCRIPTION: SEQ ID NO:18:

| | | | | | |
|---|---|---|---|---|---|
| tttcgtgtga | gtccagtgct | aatagctcat | actatatcag | aatatcacca gttcctctaa | 60 |
| ttcacttata | gtttaacact | tgagtagctt | gctttgccaa | agttatttca tggatgaata | 120 |
| atatcatcct | aacttgcctc | ttctactcat | tcttggaagG | TATACCTGGA GTTTCAGGGC | 180 |
| CAAAAGGTTA | TCAGGGTTTG | CCTGGAGACC | CAGGGCAACC | TGGACTGAGT GGACAACCTG | 240 |
| GATTACCAGG | ACCACCAGgt | aagtgtgata | ggccatttgt | agcaattgct tagctgacac | 300 |
| tgaattc | | | | | 307 |

(2) INFORMATION FOR SEQ ID NO:19:

(i) SEQUENCE CHARACTERISTICS:
        (A) LENGTH:         304 base pairs
        (B) TYPE:           Nucleic acid
        (C) STRANDEDNESS:   Single
        (D) TOPOLOGY:      Linear (ii) MOLECULE TYPE:       Nucleotide-genomic DNA (iii) HYPOTHETICAL:       Irrelevant (iv) ANTI-SENSE:         Irrelevant (v) FRAGMENT TYPE:       Endonuclease restriction
        fragment (vi) ORIGINAL SOURCE:
        (A) ORGANISM:      Human
        (B) STRAIN:        Irrelevant
        (C) INDIVIDUAL ISOLATE: Irrelevant
        (D) DEVELOPMENTAL STAGE: Irrelevant
        (E) HAPLOTYPE:      Irrelevant
        (F) TISSUE TYPE:    Liver
        (G) CELL TYPE:      Irrelevant
        (H) CELL LINE:      Irrelevant
        (I) ORGANELLE:      Irrelevant (vii) IMMEDIATE SOURCE:
        (A) LIBRARY:       Human genomic library
            (lambda FIX, Stratagene, CA)
        (B) CLONE:         F8

(viii) POSITION IN GENOME:
        (A) CHROMOSOME/SEGMENT:    X
        (B) MAP POSITION:   q22
        (C) UNITS:         Irrelevant (ix) FEATURE:
        (A) NAME/KEY:       COL4A5 collagen gene
        (B) LOCATION:      Exon 19 region from 3'
            end of gene
        (C) IDENTIFICATION METHOD:DNA sequencing
        (D) OTHER INFORMATION:   The sequence contains 71
            nucleotides from intron 19 (lower case letters),
            150 nucleotides of exon 19 (capital letters) and
            83 nucleotides of intron 18 (lower case letters).

(x) SEQUENCE DESCRIPTION: SEQ ID NO:19:

| | | | | | |
|---|---|---|---|---|---|
| ataatcttta | tatgcattaa | tctttgatgg | ataaaattga | tatattgtgt ttcacacac | 60 |
| attgatttta | gGTGATGATG | GCTTGCAGGG | TCAGCCAGGA | CTTCCTGGCC CTACAGGAGA | 120 |
| AAAAGGTAGT | AAAGGAGAGC | CTGGCCTTCC | AGGCCCTCCTG | GACCAATGGA TCCAAATCT | 180 |
| TCTGGGCTCA | AAAGGAGAGA | AGGGGGAACC | TGGCTTACCAG | gtgagtgaat gaatttatt | 240 |
| tatgaatatt | tttcctgata | tatctgaagt | ttaattttaa | atagcatgaa aagtgactt | 300 |
| ataa | | | | | 304 |

```
(2) INFORMATION FOR SEQ ID NO:20:

(i) SEQUENCE CHARACTERISTICS:
        (A) LENGTH:              28
        (B) TYPE:                Nucleic acid
        (C) STRANDEDNESS:        Single
        (D) TOPOLOGY:            Linear (ii) MOLECULE TYPE:                   Nucleotide-genomic DNA (iii) HYPOTHETICAL:                   Irrelevant (iv) ANTI-SENSE:                      Irrelevant (x) SEQUENCE DESCRIPTION:             SEQ ID NO:20:

CTAGAATTCG GTGAGCCTTG GTCTGCCT                                            28

(2) INFORMATION FOR SEQ ID NO:21:

(i) SEQUENCE CHARACTERISTICS:
        (A) LENGTH:              27
        (B) TYPE:                Nucleic acid
        (C) STRANDEDNESS:        Single
        (D) TOPOLOGY:            Linear (ii) MOLECULE TYPE:                   Nucleotide-genomic DNA (iii) HYPOTHETICAL:                   Irrelevant (iv) ANTI-SENSE:                      Irrelevant (x) SEQUENCE DESCRIPTION:             SEQ ID NO:21:

CCGAAGCTTC TGGGAATCCA GGAAGGC                                             27

(2) INFORMATION FOR SEQ ID NO:22:

(i) SEQUENCE CHARACTERISTICS:
        (A) LENGTH:              27
        (B) TYPE:                Nucleic acid
        (C) STRANDEDNESS:        Single
        (D) TOPOLOGY:            Linear (ii) MOLECULE TYPE:                   Nucleotide-genomic DNA (iii) HYPOTHETICAL:                   Irrelevant (iv) ANTI-SENSE:                      Irrelevant (x) SEQUENCE DESCRIPTION:             SEQ ID NO:22:

GACTCTAGAA AGGCCATTGC ACTGGTT                                             27

(2) INFORMATION FOR SEQ ID NO:23:

(i) SEQUENCE CHARACTERISTICS:
        (A) LENGTH:              27
        (B) TYPE:                Nucleic acid
        (C) STRANDEDNESS:        Single
        (D) TOPOLOGY:            Linear (ii) MOLECULE TYPE:                   Nucleotide-genomic DNA (iii) HYPOTHETICAL:                   Irrelevant (iv) ANTI-SENSE:                      Irrelevant (x) SEQUENCE DESCRIPTION:             SEQ ID NO:23:

AGCGAATTCC TGACCTGAGT CATGTAT                                             27
```